US012679887B2

(12) United States Patent

Li et al.

(10) Patent No.: US 12,679,887 B2

(45) Date of Patent: Jul. 14, 2026

(54) ANTI-INTERLEUKIN-17A ANTIBODY, PHARMACEUTICAL COMPOSITION THEREOF AND USE THEREOF

(71) Applicant: Akeso Biopharma, Inc., Zhongshan (CN)

(72) Inventors: Baiyong Li, Zhongshan (CN); Yu Xia, Zhongshan (CN); Zhongmin Maxwell Wang, Zhongshan (CN); Peng Zhang, Zhongshan (CN)

(73) Assignee: Akeso Biopharma, Inc., Zhongshan (CN)

( * ) Notice: Subject to any disclaimer, the term of this patent is extended or adjusted under 35 U.S.C. 154(b) by 1198 days.

(21) Appl. No.: 17/055,252

(22) PCT Filed: May 24, 2019

(86) PCT No.: PCT/CN2019/088344

§ 371 (c)(1),
(2) Date: Nov. 13, 2020

(87) PCT Pub. No.: WO2019/228266

PCT Pub. Date: Dec. 5, 2019

(65) Prior Publication Data

US 2021/0122815 A1 Apr. 29, 2021

(30) Foreign Application Priority Data

May 30, 2018 (CN) ......................... 201810539405.0

(51) Int. Cl.
| | |
|---|---|
| *C07K 16/24* | (2006.01) |
| *A61K 47/68* | (2017.01) |
| *A61P 17/06* | (2006.01) |
| *G01N 33/577* | (2006.01) |

(52) U.S. Cl.
CPC ........ *C07K 16/244* (2013.01); *A61K 47/6801* (2017.08); *A61P 17/06* (2018.01); *G01N 33/577* (2013.01)

(58) Field of Classification Search
CPC ... C07K 16/244; A61K 47/6801; A61P 17/06; G01N 33/577
See application file for complete search history.

(56) References Cited

U.S. PATENT DOCUMENTS

| | | | |
|---|---|---|---|
| 4,816,567 A | 3/1989 | Cabilly et al. | |
| 10,442,857 B2 | 10/2019 | Ulitin et al. | |
| 10,738,112 B2 | 8/2020 | Zhang et al. | |
| 2011/0293629 A1* | 12/2011 | Bastid ................. | C07K 16/244 435/7.1 |
| 2017/0327571 A1 | 11/2017 | Liu et al. | |

FOREIGN PATENT DOCUMENTS

| | | |
|---|---|---|
| CN | 105315371 A | 2/2016 |
| CN | 106795219 A | 5/2017 |
| CN | 107488227 A | 12/2017 |
| WO | WO-2006013107 A1 | 2/2006 |
| WO | WO-2007070750 A1 | 6/2007 |
| WO | WO-2009147362 A1 | 12/2009 |
| WO | WO-2012059598 A2 | 5/2012 |
| WO | WO-2014001368 A1 | 1/2014 |
| WO | WO-2014122613 A1 | 8/2014 |
| WO | WO-2014161570 A1 | 10/2014 |
| WO | WO-2016082193 A1 | 6/2016 |
| WO | WO-2016113555 A1 | 7/2016 |
| WO | WO-2017221174 A1 | 12/2017 |

OTHER PUBLICATIONS

Paul, Fundamental Immunology, 3rd Edition, 1993, pp. 292-295 (Year: 1993).*

Bendig M. M. (Methods: A Companion to Methods in Enzymology, 1995; 8:83-93) (Year: 1995).*

Rudikoff et al. (Proceedings of the National Academy of Sciences USA, vol. 79, p. 1979-1983, 1982) (Year: 1982).*

Dubel (Handbook of Therapeutic Antibodies, 2007, p. 100-101) (Year: 2007).*

Johnson and Wu (Methods in Molecular Biology, Antibody Engineering: Methods and Protocols, vol. 248, p. 11-25, 2004) (Year: 2004).*

Rothstein et al., "Secukinumab for treating plaque psoriasis," Expert Opinion on Biology Therapy 16(1):119-128 (2015).

Strober et al, "Secukinumab improves patient-reported psoriasis symptoms of itching, pain, and scaling: results of two phase 3, randomized, placebo-controlled clinical trials," International Journal of Dermatology, Wiley-Blackwell publishing Ltd, UK, 55(4):401-407 (2016).

Alfthan et al., "Properties of a single-chain antibody containing different linker peptides," Protein Eng. 8(7):725-731 (1995).

Baeten et al., "Secukinumab, an Interleukin-17A Inhibitor, in Ankylosing Spondylitis," N Engl J Med, 373:253425-48 (2015).

(Continued)

*Primary Examiner* — Mary Maille Lyons

(74) *Attorney, Agent, or Firm* — COOLEY LLP

(57) ABSTRACT

The present invention relates to the fields of treating autoimmune diseases and molecular immunology, and specifically, to an anti-IL-17A antibody, a pharmaceutical composition thereof, and use thereof. The present invention relates to a monoclonal antibody or an antigen binding fragment thereof, wherein a heavy chain variable region of the monoclonal antibody comprises: HCDR1-HCDR3 with amino acid sequences set forth in SEQ ID NOs: 31-33 respectively, or HCDR1-HCDR3 with amino acid sequences set forth in SEQ ID NOs: 37-39 respectively, and a light chain variable region of the monoclonal antibody comprises: LCDR1-LCDR3 with amino acid sequences set forth in SEQ ID NOs: 34-36 respectively, or LCDR1-LCDR3 with amino acid sequences set forth in SEQ ID NOs: 40-42 respectively. Monoclonal antibodies of the present invention can specifically antagonize the binding of IL-17A to a ligand and inhibit activation of fibroblasts by IL-17A.

10 Claims, 17 Drawing Sheets

Specification includes a Sequence Listing.

(56)                 References Cited

OTHER PUBLICATIONS

Bird et al., "Single-chain antigen-binding proteins," Science 242:423 426 (1988).

Chao et al., "Anti-IL-17A therapy protects against bone erosion in experimental models of rheumatoid arthritis," Autoimmunity. 44(3):243-52 (2011).

Chen et al., Plasma IL-17A is increased in new-onset SLE patients and associated with disease activity. J Clin Immunol, 30:221-225 (2010).

Choi et al. "Recombinant chimeric OKT3 scFv IgM antibodies mediate immune suppression while reducing T cell activation in vitro," Eur. J. Immunol. 31: 94-106 (2001).

Clark, "Antibody humanization: a case of the Emperor's new clothes?" Immunol. Today 21:397-402 (2000).

Dong et al., "IL-17 induces autoantibody overproduction and peripheral blood mononuclear cell overexpression of IL-6 in lupus nephritis patients," Chin Med J (Engl), 116(4):543-548 (2003).

Dubin et al., "Interleukin-17A and interleukin-17F: a tale of two cytokines," Immunity 30(1): 9-11 (2009).

Ely et al., Structural basis of receptor sharing by interleukin 17 cytokines, Nat Immunol 10(12): 1245-1251 (2009).

Gaffen, "The role of interleukin-17 in the pathogenesis of rheumatoid arthritis," Curr Rheumatol Rep 11:365-370 (2009).

Gaffen et al., "Structure and signalling in the IL-17 receptor superfamily," Nat Rev Immunol 9:556-567 (2009).

Genbank Accession No. p01834, dated Apr. 7, 2021, 6 pages.

Genbank Accession No. P01857, dated Apr. 7, 2021, 9 pages.

GenBank ID: Q16552, dated Apr. 7, 2021, 9 pages.

Genbank No. NP_055154.3, dated May 6, 2021, 4 pages.

Gottlieb et al., "Secukinumab Improves Physical Function in Subjects With Plaque Psoriasis and Psoriatic Arthritis: Results from Two Randomized, Phase 3 Trials," J Drugs Dermatol, 14821-14833 (2015).

Gracey et al., "Sexual Dimorphism in the Th17 Signature of Ankylosing Spondylitis," Arthritis R.heumatoL 68(3): 679-689. (2016).

Holliger et al., "'Diabodie': small bivalent and bispecific antibody fragments," Proc. Natl. Acad. Sci. USA 90(14): 6444-6448 (1993).

Hu et al., "Minibody: A novel engineered anti-carcinoembryonic antigen antibody fragment (single-chain Fv-CH3) which exhibits rapid, high-level targeting of xenografts," Cancer Res. 56:3055-3061 (1996).

Huston et al., "Protein engineering of antibody binding sites: recovery of specific activity in an anti-digoxin single-chain Fv analogue produced in *Escherichia coli*," Proc. Natl. Acad. Sci. USA 85:5879-5883 (1988).

Hymowitz et al., "IL-17s adopt a cystine knot fold: structure and activity of a novel cytokine, IL-17F, and implications for receptor binding," EMBO J. 20(19):5332-5341 (2001).

Johansen et al., "Characterization of the interleukin-17 isoforms and receptors in lesional psoriatic skin," Brit J Dermatol, 160(2):319-324 (2009).

Jones et al., "Replacing the complementarity-determining regions in a human antibody with those from a mouse," Nature, 321:522-525 (1986).

Kipriyanov et al., "Bispecific tandem diabody for tumor therapy with improved antigen binding and pharmacokinetics," J. Mol. Biol. 293(1):41-56 (1999).

Kitami et al., "IL-17A suppresses the expression of bone resorption-related proteinases and osteoclast differentiation via IL-17RA or IL-17RC receptors in RAW264.7 cells," Biochimie. 92(4): 398-404 (2010).

Kohler et al., Continuous cultures of fused cells secreting antibody of predefined specificity Nature, 256(5517):495-497(1975).

Langley et al., "Secukinumab in plaque psoriasis—results of two phase 3 trials,Lowes et al., Psoriasis vulgaris lesions contain discrete populations of Th1 and Th 17 T cells," N Engl J Med, 371:326-338 (2014).

Lowes et al., "Psoriasis vulgaris lesions contain discrete populations of Th1 and Th 17 T cells," J Invest Dermatol 128(5):1207-1211 (2008).

Lubberts et al., "Overexpression of IL-17 in the knee joint of collagen type II immunized mice promotes collagen arthritis and aggravates joint destruction," Inflamm Res 51. 102-104 (2002).

Nakae et al., "Suppression of immune induction of collagen-induced arthritis in IL-17-deficient mice," J Immunol, 171(11): 6173-6177 (2003).

Nestle et al., "Psoriasis," N Engl J Med, 361. 496-509 (2009).

Ogura et al., "Interleukin-17 Promotes Autoimmunity by Triggering a Positive-Feedback Loop via Interleukin-6 Induction," Immunity 29: 628-636 (2008).

Onishi et al., "nterleukin-17 and its target genes: mechanisms of interleukin-17 function in disease," Immunology 129(3): 311-321 (2010).

Poljak RJ et al., "Production and structure of diabodies," Structure 2:1121 1123 (1994).

Presta, "Antibody engineering," Current Opinion in Structural Biology 2(4):593-596 (1992).

Reichmann et al., "Reshaping human antibodies for therapy," Nature, 332(6162):323-329 (1988).

Roovers, et al., "In vitro characterisation of a monovalent and bivalent form of a fully human anti Ep-CAM phage antibody," Cancer Immunol Immunotherapy 50(1):51-59 (2001).

Sarkar et al., "Interleukin (IL)-17A, F and AF in inflammation: a study in collagen-induced arthritis and rheumatoid arthritis," Clin Exp Immunol. 177(3): 652-661 (2014).

Shi et aL, IL-17 Signaling and Function, Chinese Journal of Cell Biology 33(4):345-357 (2011).

Toy et al., "Cutting edge: interleukin 17 signals through a heteromeric receptor complex," J Immunol 177: 36-39 (2006).

Ward et al., "Binding activities of a repertoire of single immunoglobulin variable domains secreted from *Escherichia coli*," Nature 341:544 546 (1989).

Wright et al, "The human IL-17F/IL-17A heterodimeric cytokine signals through the IL-17RA/IL-17RC receptor complex," J Immunol 181: 2799-2805 (2008).

Mirsky, A, et al., "Antibody-Specific Model of Amino Acid Substitution for Immunological Inferences from Alignments of Antibody Sequences" Mol. Biol. Evol. 32(3): 806-819 Mar. 2015.

IN Application No. 202017056968, Office Action mailed Mar. 24, 2026; Applicant AKESO Biopharma, INC., 9 total pages including English translation.

* cited by examiner

SEQUENCE LISTING

```
<160> NUMBER OF SEQ ID NOS: 51

<210> SEQ ID NO 1
<211> LENGTH: 360
<212> TYPE: DNA
<213> ORGANISM: Artificial Sequence
<220> FEATURE:
<223> OTHER INFORMATION: Synthetic Sequence

<400> SEQUENCE: 1
gaagtaaagc tgcaggagtc gggacctggc ctggtgaaac cttctcagtc tctgtccctc       60
acctgcactg tcactagcta ctcattcacc agtgattatg cctggagctg gatccggcag      120
tttccaggaa tcaaactgga gtggatgggc tacataacct acagtggtgt cactagctac      180
aacccctctc tcaaaagtcg aatctctatc actcgagaca catccaagaa ccagttcttc      240
ctacagttga attctgtgac tactgaggac acggccacat attactgtgc aagggcagac      300
tatgatagct actatactat ggactactgg ggtcaaggaa cctcagtcac cgtctcctca      360

<210> SEQ ID NO 2
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 2

Glu Val Lys Leu Gln Glu Ser Gly Pro Gly Leu Val Lys Pro Ser Gln
1               5                   10                  15

Ser Leu Ser Leu Thr Cys Thr Val Thr Ser Tyr Ser Phe Thr Ser Asp
            20                  25                  30

Tyr Ala Trp Ser Trp Ile Arg Gln Phe Pro Gly Ile Lys Leu Glu Trp
        35                  40                  45

Met Gly Tyr Ile Thr Tyr Ser Gly Val Thr Ser Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ala Asp Tyr Asp Ser Tyr Tyr Thr Met Asp Tyr Trp Gly Gln
            100                 105                 110

Gly Thr Ser Val Thr Val Ser Ser
        115                 120

<210> SEQ ID NO 3
<211> LENGTH: 333
<212> TYPE: DNA
<213> ORGANISM: Artificial Sequence
```

<220> FEATURE:
<223> OTHER INFORMATION: Synthetic Sequence

<400> SEQUENCE: 3
gacatccagc tgactcagtc tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaagg ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatttttgg     300
acgttcggtg gaggcaccaa gctggaaata aaa                                  333

<210> SEQ ID NO 4
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 4

Asp Ile Gln Leu Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Trp Thr Phe Gly Gly Gly Thr Lys Leu Glu Ile Lys
            100                 105                 110

<210> SEQ ID NO 5
<211> LENGTH: 360
<212> TYPE: DNA
<213> ORGANISM: Artificial Sequence
<220> FEATURE:
<223> OTHER INFORMATION: Synthetic Sequence

<400> SEQUENCE: 5
gatgtgcagc tgcaggaaag cggaccagga ctggtgaagc ctagccagac cctgagcctg      60
acttgcaccg tgtccagcta cagcttcacc agcgactacg cttggtcttg gatcagacag     120
ttcccaggaa ttggcctcga gtggatgggc tacatcacct acagcggcgt gaccagctac     180
aaccccagcc tgaagagcag gatcaccatc agccgggaca ccagcaagaa ccagttcttc     240
ctgcagctga caagcgtgac agcagccgat accgcagtgt actattgcgc cagggccgac     300
tacgacagct actacaccat ggactattgg ggccagggaa ccagcgtgac agtgtctagc     360

<210> SEQ ID NO 6
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 6

-continued

```
Asp Val Gln Leu Gln Glu Ser Gly Pro Gly Leu Val Lys Pro Ser Gln
1               5                   10                  15

Thr Leu Ser Leu Thr Cys Thr Val Ser Ser Tyr Ser Phe Thr Ser Asp
            20                  25                  30

Tyr Ala Trp Ser Trp Ile Arg Gln Phe Pro Gly Ile Gly Leu Glu Trp
        35                  40                  45

Met Gly Tyr Ile Thr Tyr Ser Gly Val Thr Ser Tyr Asn Pro Ser Leu
    50                  55                  60

Lys Ser Arg Ile Thr Ile Ser Arg Asp Thr Ser Lys Asn Gln Phe Phe
65                  70                  75                  80

Leu Gln Leu Asn Ser Val Thr Ala Ala Asp Thr Ala Val Tyr Tyr Cys
                85                  90                  95

Ala Arg Ala Asp Tyr Asp Ser Tyr Tyr Thr Met Asp Tyr Trp Gly Gln
            100                 105                 110

Gly Thr Ser Val Thr Val Ser Ser
        115                 120
```

```
<210> SEQ ID NO 7
<211> LENGTH: 333
<212> TYPE: DNA
<213> ORGANISM: Artificial Sequence
<220> FEATURE:
<223> OTHER INFORMATION: Synthetic Sequence

<400> SEQUENCE: 7
gatgtcgtga tgacccagac ccctctgtct ctgccagtga cactgggaca gcaggctagc      60
atctcttgca gaagcagcca gagcctggtg cacagcaacg gcaacaccta cctgcattgg     120
tacctgcaga agccaggcca gtctcctaga ctgctgatct acaaggtgtc caaccggttc     180
agcggcgtgc cagatagatt cagcggaagc ggaagcggca ccgacttcac cctgaagatc     240
agcagagtgg aggccgagga tctgggagtg tacttctgca gccagagcac ccactttttgg    300 accttcggcg gaggcaccaa gctggagatc aag                                  333
```

```
<210> SEQ ID NO 8
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 8

Asp Val Val Met Thr Gln Thr Pro Leu Ser Leu Pro Val Thr Leu Gly
1               5                   10                  15

Gln Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Trp Thr Phe Gly Gly Gly Thr Lys Leu Glu Ile Lys
            100                 105                 110
```

<210> SEQ ID NO 9
<211> LENGTH: 360
<212> TYPE: DNA
<213> ORGANISM: Artificial Sequence
<220> FEATURE:
<223> OTHER INFORMATION: Synthetic Sequence

<400> SEQUENCE: 9
gatgtgcagc tgcaggaaag cggaccagga ctggtgaagc ctagccagac cctgagcctg      60
acttgcaccg tgtccagcta cagcttcacc agcgactacg cttggtcttg gatcagacag     120
ccaccaggaa agggactcga gtggatcggc tacatcacct acagcggcgt gaccagctac     180 aacccccagcc tgaagagcag gatcaccatc agccgggaca ccagcaagaa ccagttcttc    240
ctgcagctgt ctagcgtgac agcagccgat accgcagtgt actattgcgc cagggccgac     300
tacgacagct actacaccat ggactattgg ggccagggaa ccagcgtgac agtgtctagc      360

<210> SEQ ID NO 10
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 10

Asp Val Gln Leu Gln Glu Ser Gly Pro Gly Leu Val Lys Pro Ser Gln
1               5                   10                  15

Thr Leu Ser Leu Thr Cys Thr Val Ser Ser Tyr Ser Phe Thr Ser Asp
            20                  25                  30

Tyr Ala Trp Ser Trp Ile Arg Gln Pro Pro Gly Lys Gly Leu Glu Trp
        35                  40                  45

Ile Gly Tyr Ile Thr Tyr Ser Gly Val Thr Ser Tyr Asn Pro Ser Leu
    50                  55                  60

Lys Ser Arg Ile Thr Ile Ser Arg Asp Thr Ser Lys Asn Gln Phe Phe
65                  70                  75                  80

Leu Gln Leu Ser Ser Val Thr Ala Ala Asp Thr Ala Val Tyr Tyr Cys
                85                  90                  95

Ala Arg Ala Asp Tyr Asp Ser Tyr Tyr Thr Met Asp Tyr Trp Gly Gln
            100                 105                 110

Gly Thr Ser Val Thr Val Ser Ser
        115                 120

<210> SEQ ID NO 11
<211> LENGTH: 333
<212> TYPE: DNA
<213> ORGANISM: Artificial Sequence
<220> FEATURE:
<223> OTHER INFORMATION: Synthetic Sequence

<400> SEQUENCE: 11
gatgtcgtga tgacccagac ccctctgtct ctgccagtga cactgggaca gccagctagc      60
atctcttgca gaagcagcca gagcctggtg cacagcaacg gcaacaccta cctgcattgg     120
tacctgcaga agccaggcca gtctcctaga ctgctgatct acaaggtgtc caaccggttc     180
agcggcgtgc cagatagatt cagcggaagc ggaagcggca ccgacttcac cctgaagatc     240
agcagagtgg aggccgagga tctgggagtg tactactgca gccagagcac ccactttttgg    300 accttcggcg gaggcaccaa gctggagatc aag                                  333

<210> SEQ ID NO 12

```
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 12

Asp Val Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Ser Gln Ser
                85                  90                  95

Thr His Phe Trp Thr Phe Gly Gly Gly Thr Lys Leu Glu Ile Lys
                100                 105                 110

<210> SEQ ID NO 13
<211> LENGTH: 360
<212> TYPE: DNA
<213> ORGANISM: Artificial Sequence
<220> FEATURE:
<223> OTHER INFORMATION: Synthetic Sequence

<400> SEQUENCE: 13
gatgtgcagc tgcaggaaag cggaccagga ctggtgaagc ctagccagac cctgagcctg      60
acttgcaccg tgtccagcta cagcttcacc agcgactacg cttggtcttg gatcagacag     120
ccaccaggaa agggactcga gtggatcggc tacatcacct acagcggcgt gaccagctac     180
aaccctagcc tgaagagccg cgtgaccatt agcgtggaca ccagcaagaa ccagttctcc     240
ctgaagctga gcagcgtgac agccgccgat acagcagtgt actattgcgc ccgggccgat     300
tacgacagct actacaccat ggactattgg ggccagggaa ccagcgtgac agtgtctagc     360

<210> SEQ ID NO 14
<211> LENGTH: 120
<212> TYPE: PRT
<213> ORGANISM: Artificial Sequence
<220> FEATURE:
<223> OTHER INFORMATION: Synthetic Sequence

<400> SEQUENCE: 14

Asp Val Gln Leu Gln Glu Ser Gly Pro Gly Leu Val Lys Pro Ser Gln
1               5                   10                  15

Thr Leu Ser Leu Thr Cys Thr Val Ser Ser Tyr Ser Phe Thr Ser Asp
            20                  25                  30

Tyr Ala Trp Ser Trp Ile Arg Gln Pro Pro Gly Lys Gly Leu Glu Trp
        35                  40                  45

Ile Gly Tyr Ile Thr Tyr Ser Gly Val Thr Ser Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

```
Ala Arg Ala Asp Tyr Asp Ser Tyr Tyr Thr Met Asp Tyr Trp Gly Gln
            100                 105                 110

Gly Thr Ser Val Thr Val Ser Ser
        115                 120

<210> SEQ ID NO 15
<211> LENGTH: 351
<212> TYPE: DNA
<213> ORGANISM: Artificial Sequence
<220> FEATURE:
<223> OTHER INFORMATION: Synthetic Sequence

<400> SEQUENCE: 15
gaggttcagc tggagcagtc tggttctgaa ctgaggagtc ctggatcttc agtaaagctt      60
tcatgcaagg attttgattc agaagtcttc cctattgctg atatgagttg ggttaggcag     120
aagcctgggc atggatttga atggattgga gacatactcc caagttttgg tagaacaatc     180
tatggagaga gttttgagga caaagccaaa gtggatgcag acacagtgtc caacacagcc     240
tacttggaac tcaacagtct gacatctgag gactctgcta tctactactg tgcaggggggt     300 aactacgggt ttgcttactg gggccaaggg actctggtca ctgtctctgc a              351

<210> SEQ ID NO 16
<211> LENGTH: 117
<212> TYPE: PRT
<213> ORGANISM: Artificial Sequence
<220> FEATURE:
<223> OTHER INFORMATION: Synthetic Sequence

<400> SEQUENCE: 16

Glu Val Gln Leu Glu Gln Ser Gly Ser Glu Leu Arg Ser Pro Gly Ser
1               5                   10                  15

Ser Val Lys Leu Ser Cys Lys Asp Phe Asp Ser Glu Val Phe Pro Ile
            20                  25                  30

Ala Asp Met Ser Trp Val Arg Gln Lys Pro Gly His Gly Phe Glu Trp
        35                  40                  45

Ile Gly Asp Ile Leu Pro Ser Phe Gly Arg Thr Ile Tyr Gly Glu Lys
    50                  55                  60

Phe Glu Asp Lys Ala Lys Val Asp Ala Asp Thr Val Ser Asn Thr Ala
65                  70                  75                  80

Tyr Leu Glu Leu Asn Ser Leu Thr Ser Glu Asp Ser Ala Ile Tyr Tyr
                85                  90                  95

Cys Ala Arg Gly Asn Tyr Gly Phe Ala Tyr Trp Gly Gln Gly Thr Leu
            100                 105                 110

Val Thr Val Ser Ala
        115

<210> SEQ ID NO 17
<211> LENGTH: 336
<212> TYPE: DNA
<213> ORGANISM: Artificial Sequence
<220> FEATURE:
<223> OTHER INFORMATION: Synthetic Sequence

<400> SEQUENCE: 17
gatgttttga tgacccaaac tccactcact ttgtcggtta tcattggaca accagcctcc      60
atctcttgca agccaagtca gagcctctta aatagtgatg gaaagacata tttgaattgg     120
ttgttgcaga ggccaggcca gtctccaaag cgcctaatct atctggtgtc taaactggac     180
tctggagtcc ctgacaggtt cactggcagt ggatcaggga cagatttcac actgaaaatc     240
```

-continued

```
agcagagtgg aggctgagga tttgggagtt tattattgct ggcaaggttc acattttcct    300
cagacgttcg gtggaggcac aaagttggaa ataaaa                              336
```

<210> SEQ ID NO 18
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 18

```
Asp Val Leu Met Thr Gln Thr Pro Leu Thr Leu Ser Val Ile Ile Gly
1               5                   10                  15

Gln Pro Ala Ser Ile Ser Cys Lys Pro Ser Gln Ser Leu Leu Asn Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ser His Phe Pro Gln Thr Phe Gly Gly Gly Thr Lys Leu Glu Ile Lys
            100                 105                 110
```

<210> SEQ ID NO 19
<211> LENGTH: 348
<212> TYPE: DNA
<213> ORGANISM: Artificial Sequence
<220> FEATURE:
<223> OTHER INFORMATION: Synthetic Sequence

<400> SEQUENCE: 19

```
gtgcagctgg tgcagagcgg aagcgaactg agaaagccag gctccagcgt gaagctgtct     60
tgcaaggact cgacagcga ggtgttcccc atcgccgata tgtcttgggt ccgacaggct    120
ccaggccagg gattcgagtg gatcggtgac attctgccca gcttcggaag aaccaactac    180
gcccagaagt tcgagggcaa ggccaaggtg acgcagaca agagcaccaa caccgcctac    240
ctggagctga acagcctgag aagcgaggac accgccatct actattgcgc caggggcaac    300
tacggattcg cctattgggg ccagggaaca ctggtgacag tgtccgcc                 348
```

<210> SEQ ID NO 20
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 20

```
Val Gln Leu Val Gln Ser Gly Ser Glu Leu Arg Lys Pro Gly Ser Ser
1               5                   10                  15

Val Lys Leu Ser Cys Lys Asp Phe Asp Ser Glu Val Phe Pro Ile Ala
            20                  25                  30

Asp Met Ser Trp Val Arg Gln Ala Pro Gly Gln Gly Phe Glu Trp Ile
        35                  40                  45

Gly Asp Ile Leu Pro Ser Phe Gly Arg Thr Asn Tyr Ala Gln Lys Phe
    50                  55                  60
```

-continued

```
Glu Gly Lys Ala Lys Val Asp Ala Asp Lys Ser Thr Asn Thr Ala Tyr
65                  70                  75                  80

Leu Glu Leu Asn Ser Leu Arg Ser Glu Asp Thr Ala Ile Tyr Tyr Cys
                85                  90                  95

Ala Arg Gly Asn Tyr Gly Phe Ala Tyr Trp Gly Gln Gly Thr Leu Val
            100                 105                 110

Thr Val Ser Ala
        115
```

```
<210> SEQ ID NO 21
<211> LENGTH: 336
<212> TYPE: DNA
<213> ORGANISM: Artificial Sequence
<220> FEATURE:
<223> OTHER INFORMATION: Synthetic Sequence

<400> SEQUENCE: 21
gatgtcgtga tgacccagac ccctctgtct ctgagcgtga cactgggaca gccagctagc      60
atcagctgca gaagcagcca gagcctgctg aacagcgacg gcaagaccta cctgaattgg     120
ctgctgcaga gaccaggcca gtctcctaga aggctgatct acctggtgtc caagctggac     180
agcggcgtgc cagatagatt cagcggaagc ggaagcggca ccgacttcac cctgaagatc     240
agcagagtgg aggccgagga tctgggagtg tactactgtt ggcagggcag ccacttccct     300
cagacattcg gcggcggcac aaagctggag atcaag                              336
```

```
<210> SEQ ID NO 22
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 22

Asp Val Val Met Thr Gln Thr Pro Leu Ser Leu Ser Val Thr Leu Gly
1               5                   10                  15

Gln Pro Ala Ser Ile Ser Cys Arg Ser Ser Gln Ser Leu Leu Asn Ser
            20                  25                  30

Asp Gly Lys Thr Tyr Leu Asn Trp Leu Leu Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ser His Phe Pro Gln Thr Phe Gly Gly Gly Thr Lys Leu Glu Ile Lys
            100                 105                 110
```

```
<210> SEQ ID NO 23
<211> LENGTH: 348
<212> TYPE: DNA
<213> ORGANISM: Artificial Sequence
<220> FEATURE:
<223> OTHER INFORMATION: Synthetic Sequence

<400> SEQUENCE: 23
gtgcagctgg tgcagagcgg agcagaagtg aagaagccag gctccagcgt gaagctgtct      60
tgcaaggact tcgacagcga ggtgttcccc atcgccgata tgtcttgggt ccgacaggct     120
```

-continued

```
ccaggccagg gattcgagtg gatcggtgac attctgccca gcttcgggag aaccaattac    180
gcccagaagt tccagggcag agtgaccgtg accgcagaca agagcaccaa caccgcctac    240
ctggagctga acagcctgag gagcgaggat accgccgtgt actattgcgc cagggggcaac    300 tacggcttcg cctattgggg acagggaaca ctggtgacag tgtccgcc               348
```

```
<210> SEQ ID NO 24
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 24

Val Gln Leu Val Gln Ser Gly Ala Glu Val Lys Lys Pro Gly Ser Ser
1               5                   10                  15

Val Lys Leu Ser Cys Lys Asp Phe Asp Ser Glu Val Phe Pro Ile Ala
            20                  25                  30

Asp Met Ser Trp Val Arg Gln Ala Pro Gly Gln Gly Phe Glu Trp Ile
        35                  40                  45

Gly Asp Ile Leu Pro Ser Phe Gly Arg Thr Asn Tyr Ala Gln Lys Phe
    50                  55                  60

Gln Gly Arg Val Thr Val Thr Ala Asp Lys Ser Thr Asn Thr Ala Tyr
65                  70                  75                  80

Leu Glu Leu Asn Ser Leu Arg Ser Glu Asp Thr Ala Val Tyr Tyr Cys
                85                  90                  95

Ala Arg Gly Asn Tyr Gly Phe Ala Tyr Trp Gly Gln Gly Thr Leu Val
            100                 105                 110

Thr Val Ser Ala
        115
```

```
<210> SEQ ID NO 25
<211> LENGTH: 336
<212> TYPE: DNA
<213> ORGANISM: Artificial Sequence
<220> FEATURE:
<223> OTHER INFORMATION: Synthetic Sequence

<400> SEQUENCE: 25
gatgtcgtga tgacccagac ccctctgtct ctgagcgtga cactgggaca gccagctagc     60
atcagctgca gaagcagcca gagcctgctg aacagcgacg gcaagaccta cctgaattgg    120
ctgctgcaga gaccaggcca gtctcctaga aggctgatct acctggtgtc caacctggac    180
agcggcgtgc cagatagatt cagcggaagc ggaagcggca ccgacttcac cctgaagatc    240
agcagagtgg aagccgagga cgtgggagtg tactactgtt ggcagggcag ccacttccct    300
cagacattcg gcggcggcac aaagctggag atcaag                             336
```

```
<210> SEQ ID NO 26
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 26

Asp Val Val Met Thr Gln Thr Pro Leu Ser Leu Ser Val Thr Leu Gly
1               5                   10                  15

Gln Pro Ala Ser Ile Ser Cys Arg Ser Ser Gln Ser Leu Leu Asn Ser
```

-continued

```
                20                  25                  30

Asp Gly Lys Thr Tyr Leu Asn Trp Leu Leu Gln Arg Pro Gly Gln Ser
        35                  40                  45

Pro Arg Arg Leu Ile Tyr Leu Val Ser Asn Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
            85                  90                  95

Ser His Phe Pro Gln Thr Phe Gly Gly Gly Thr Lys Leu Glu Ile Lys
        100                 105                 110
```

```
<210> SEQ ID NO 27
<211> LENGTH: 348
<212> TYPE: DNA
<213> ORGANISM: Artificial Sequence
<220> FEATURE:
<223> OTHER INFORMATION: Synthetic Sequence

<400> SEQUENCE: 27
gtgcagctgg tgcagagcgg agcagaagtg aagaagccag gcagcagcgt gaaggtgtct      60
tgcaaggact tcagcagcga ggtgttcccc atcgccgata tgtcttgggt ccgacaggct     120
ccaggccagg gactggagtg gatcggtgac attctgccca gcttcgggag aaccaattac     180
gcccagaagt tccagggcag agtgaccgtg accgcagaca agagcaccaa caccgcctac     240
ctggagctgt ctagcctgag aagcgaggac accgccgtgt actattgcgc cagggcaac      300 tacggcttcg cctattgggg acagggaaca ctggtgacag tgtccgcc                  348
```

```
<210> SEQ ID NO 28
<211> LENGTH: 116
<212> TYPE: PRT
<213> ORGANISM: Artificial Sequence
<220> FEATURE:
<223> OTHER INFORMATION: Synthetic Sequence

<400> SEQUENCE: 28
```

```
Val Gln Leu Val Gln Ser Gly Ala Glu Val Lys Lys Pro Gly Ser Ser
1                   5                   10                  15

Val Lys Val Ser Cys Lys Asp Phe Ser Ser Glu Val Phe Pro Ile Ala
            20                  25                  30

Asp Met Ser Trp Val Arg Gln Ala Pro Gly Gln Gly Leu Glu Trp Ile
        35                  40                  45

Gly Asp Ile Leu Pro Ser Phe Gly Arg Thr Asn Tyr Ala Gln Lys Phe
    50                  55                  60

Gln Gly Arg Val Thr Val Thr Ala Asp Lys Ser Thr Asn Thr Ala Tyr
65                  70                  75                  80

Leu Glu Leu Ser Ser Leu Arg Ser Glu Asp Thr Ala Val Tyr Tyr Cys
            85                  90                  95

Ala Arg Gly Asn Tyr Gly Phe Ala Tyr Trp Gly Gln Gly Thr Leu Val
        100                 105                 110

Thr Val Ser Ala
        115
```

```
<210> SEQ ID NO 29
<211> LENGTH: 336
<212> TYPE: DNA
<213> ORGANISM: Artificial Sequence
<220> FEATURE:
```

<223> OTHER INFORMATION: Synthetic Sequence

<400> SEQUENCE: 29
gatgtcgtga tgacccagac ccctctgtct ctgagcgtga cactgggaca gccagctagc      60
atcagctgca gaagcagcca gagcctgctg aacagcgacg gcaagaccta cctgaattgg     120
ttcctgcaga gaccaggcca gtctcctaga aggctgatct acctggtgtc caacctggac     180
agcggcgtgc cagatagatt cagcggaagc ggaagcggca ccgacttcac cctgaagatc     240
agcagagtgg aagccgagga cgtgggagtg tactactgtt ggcagggcag ccacttccct     300
cagacattcg gcggcggcac aaagctggag atcaag                               336

<210> SEQ ID NO 30
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 30

Asp Val Val Met Thr Gln Thr Pro Leu Ser Leu Ser Val Thr Leu Gly
1               5                   10                  15

Gln Pro Ala Ser Ile Ser Cys Arg Ser Ser Gln Ser Leu Leu Asn Ser
            20                  25                  30

Asp Gly Lys Thr Tyr Leu Asn Trp Phe Leu Gln Arg Pro Gly Gln Ser
        35                  40                  45

Pro Arg Arg Leu Ile Tyr Leu Val Ser Asn Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Ser His Phe Pro Gln Thr Phe Gly Gly Gly Thr Lys Leu Glu Ile Lys
            100                 105                 110

<210> SEQ ID NO 31
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 31

Ser Tyr Ser Phe Thr Ser Asp Tyr Ala
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 32

Ile Thr Tyr Ser Gly Val Thr
1               5

<210> SEQ ID NO 33
<211> LENGTH: 13
<212> TYPE: PRT
<213> ORGANISM: Artificial Sequence
<220> FEATURE:

-continued

```
<223> OTHER INFORMATION: Synthetic Sequence

<400> SEQUENCE: 33

Ala Arg Ala Asp Tyr Asp Ser Tyr Tyr Thr Met Asp Tyr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 34

Gln Ser Leu Val His Ser Asn Gly Asn Thr Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 35

Lys Val Ser
1

<210> SEQ ID NO 36
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 36

Ser Gln Ser Thr His Phe Trp Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 37

Ser Glu Val Phe Pro Ile Ala Asp
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 38

Ile Leu Pro Ser Phe Gly Arg Thr
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic Sequence
```

<400> SEQUENCE: 39

Ala Arg Gly Asn Tyr Gly Phe Ala Tyr
1               5

<210> SEQ ID NO 40
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 40

Gln Ser Leu Leu Asn Ser Asp Gly Lys Thr Tyr
1               5                   10

<210> SEQ ID NO 41
<211> LENGTH: 3
<212> TYPE: PRT
<213> ORGANISM: Artificial Sequence
<220> FEATURE:
<223> OTHER INFORMATION: Synthetic Sequence

<400> SEQUENCE: 41

Leu Val Ser
1

<210> SEQ ID NO 42
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 42

Trp Gln Gly Ser His Phe Pro Gln Thr
1               5

<210> SEQ ID NO 43
<211> LENGTH: 155
<212> TYPE: PRT
<213> ORGANISM: Artificial Sequence
<220> FEATURE:
<223> OTHER INFORMATION: Synthetic Sequence

<400> SEQUENCE: 43

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

```
Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 44
<211> LENGTH: 5
<212> TYPE: PRT
<213> ORGANISM: Artificial Sequence
<220> FEATURE:
<223> OTHER INFORMATION: Synthetic Construct

<400> SEQUENCE: 44

Gly Gly Gly Gly Ser
1               5

<210> SEQ ID NO 45
<211> LENGTH: 20
<212> TYPE: PRT
<213> ORGANISM: Artificial Sequence
<220> FEATURE:
<223> OTHER INFORMATION: Synthetic Construct

<400> SEQUENCE: 45

Gly Gly Gly Gly Ser Gly Gly Gly Gly Ser Gly Gly Gly Gly Ser Gly
1               5                   10                  15

Gly Gly Gly Ser
            20

<210> SEQ ID NO 46
<211> LENGTH: 6
<212> TYPE: PRT
<213> ORGANISM: Artificial Sequence
<220> FEATURE:
<223> OTHER INFORMATION: Synthetic Sequence

<400> SEQUENCE: 46

Ser Asp Tyr Ala Trp Ser
1               5

<210> SEQ ID NO 47
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 47

Tyr Ile Thr Tyr Ser Gly Val Thr Ser Tyr Asn Pro Ser Leu Lys Ser
1               5                   10                  15

<210> SEQ ID NO 48
<211> LENGTH: 11
<212> TYPE: PRT
<213> ORGANISM: Artificial Sequence
<220> FEATURE:
<223> OTHER INFORMATION: Synthetic Sequence

<400> SEQUENCE: 48

Ala Asp Tyr Asp Ser Tyr Tyr Thr Met Asp Tyr
1               5                   10

<210> SEQ ID NO 49
<211> LENGTH: 16
<212> TYPE: PRT
<213> ORGANISM: Artificial Sequence
```

-continued

```
<220> FEATURE:
<223> OTHER INFORMATION: Synthetic Sequence

<400> SEQUENCE: 49

Arg Ser Ser Gln Ser Leu Val His Ser Asn Gly Asn Thr Tyr Leu His
1               5                   10                  15

<210> SEQ ID NO 50
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 50

Lys Val Ser Asn Arg Phe Ser
1               5

<210> SEQ ID NO 51
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 51

Ser Gln Ser Thr His Phe Trp Thr
1               5
```

ANTI-INTERLEUKIN-17A ANTIBODY, PHARMACEUTICAL COMPOSITION THEREOF AND USE THEREOF

RELATED APPLICATIONS

This application is a U.S. National Phase Application, filed under 35 U.S.C. § 371, of International Application No. PCT/CN2019/088344, filed on May 24, 2019, which claims priority to, and the benefit of, Chinese Application No. 201810539405.0, filed on May 30, 2018. The contents of each of the aforementioned patent applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jan. 8, 2025, is named "AKSO-005_SeqList.txt" and is about 30,877 bytes in size.

TECHNICAL FIELD

The present invention belongs to the field of molecular immunology, and relates to an anti-interleukin-17A antibody, a pharmaceutical composition thereof and use thereof. In particular, the present invention relates to an anti-interleukin-17A monoclonal antibody.

BACKGROUND

Interleukin-17A (abbreviated as IL-17A or IL 17A) is a member of IL-17 cytokine family which has 6 members, i.e. IL-17A (the IL-17A is discovered first and also called IL-17), IL-17B, IL-17C, IL-17D, IL-17E (also named as IL-25) and IL-17F (Shi Peiqing et al., Chinese Journal of Cell Biology 33:345-357 (2011)). IL-17F shares about 50% homology with IL-17A, and their coding genes are located in the same segment of chromosome 6p12 (Gaffen et al., Nat Rev Immunol 9:556-67 (2009)). IL-17A and IL-17F can exist in the form of homodimers such as IL-17A/IL-17A and IL-17F/IL-17F, as well as the heterodimer IL-17A/IL-17F. IL-17A and IL-17F exhibit biological effects by binding to receptors (Wright et al., J Immunol 181:2799-805 (2008)).

The IL-17 receptor (IL-17R) family consists of 5 members, i.e. IL-17RA, IL-17RB, IL-17RC, IL-17RD, and IL-17RE. Members of the IL-17 receptor family can form different receptor complexes, in which IL-17RA, the largest molecule discovered to date in this family, is a common subunit that transmits signals for at least four ligands, and exhibits major biological effects (Gaffen et al., Nat Rev Immunol 9:556-67 (2009)). IL-17RA and IL-17RC complex mediates cell responses to IL-17A and IL-17F (Toy et al., J Immunol 177:36-9 (2006)).

IL-17A is more critical than IL-17F in the autoimmune inflammatory response, the key reason is that IL17RA has a hundred times greater affinity for IL-17A than that for IL-17F (Ely et al., Nat Immunol 10 1245-51 (2009)), the response of a cell to IL-17A is 10 times stronger than that to IL-17F (Dubin et al., Immunity 30:9-11 (2009)). An anti-IL-17A antibody or an anti-IL-17-receptor antibody can be used to block the binding of the IL-17A to its receptor thereof, thereby blocking the biological activity of IL-17A.

IL-17A plays an important role in several autoimmune diseases (e.g. psoriasis, psoriatic arthritis, rheumatoid arthritis, ankylosing spondylitis, systemic lupus erythematosus, etc.). The anti-IL-17A monoclonal antibody Secukinumab is approved by the Food and Drug Administration (FDA) and the European Medicines Agency (EMA) for the treatment of moderate to severe plaque psoriasis, psoriatic arthritis, and ankylosing spondylitis.

Psoriasis, also known as psora, is a chronic autoimmune skin disease. The skin histological characteristics thereof are epidermal keratinocyte hyperproliferations, angiogenesis, as well as dendritic cell, macrophage, neutrophil, and T cell infiltrations. (Nestle et al., N Engl J Med, 361:496-509 (2009)). Psoriasis has various manifestations, among which plaque psoriasis is the most common type, accounting for more than 90% of all patients with psoriasis. Psoriatic arthritis (PsA) is a special type of psoriasis, which causes psoriasis rash as well as pain, swelling, tenderness, stiffness, and dyskinesia in the joints and surrounding soft tissues. Some patients may have sacroiliitis and (or) spondylitis with prolonged course, easy relapse and late-stage joint stiffness, leading to disability. The existence of psoriasis is an important difference between psoriatic arthritis and other inflammatory joint diseases, and the severity of skin lesions is not directly related to the degree of joint inflammations (Tan Zhen et al., Chinese Journal of Rheumatology 20:354-357 (2016)).

The IL-17A expression is significantly increased in psoriatic pathogenic skin tissues, and this increase is closely related to psoriasis disease activity (Johansen et al., Brit J Dermatol, 160:319-24 (2009); Lowes et al. J Invest Dermatol 128:1207-11 (2008)). Among patients with psoriasis, the anti-IL-17A monoclonal antibody Secukinumab has shown excellent efficacy, which can significantly alleviate the disease activity of patients with psoriasis and reduce the area of psoriasis plaques (Langley et al., N Engl J Med, 371:326-38 (2014)); Secukinumab can also significantly reduce arthritis symptoms and significantly improve joint functions of patients with psoriatic arthritis (Gottlieb et al., J Drugs Dermatol, 14821-33 (2015)). Secukinumab is approved by the FDA for the treatment of moderate to severe plaque psoriasis and psoriatic arthritis.

Rheumatoid arthritis (RA) is mainly characterized by inflammatory joint synovial fibroblast proliferation, joint and cartilage damage, infiltrations of CD4+ helper T cells and plasma cells producing autoantibodies. IL-17A can cause both inflammation and bone damage in rheumatoid arthritis. IL-17A is highly expressed in rheumatoid synovial monocytes of patients with rheumatoid arthritis relative to healthy people or patients with osteoarthritis (Sarkar et al., Clin Exp Immunol. 177:652-61 (2014)), cytological studies suggest that IL-17A can stimulate bone resorption and collagen destruction (Kitami et al., Biochimie. 92:398-404 (2010)). IL-17A can induce cartilage, synovial cells, macrophages and osteoblasts to secrete proinflammatory cytokines such as TNFa, IL-1b and IL-6, and exert biological effects. These proinflammatory cytokines cause sudden onset of rheumatoid arthritis and can maintain the number of TH17 cells through IL-17A-induced IL-6, thereby forming a positive feedback and acting synergistically to amplify their inflammatory effects, and establishing a chronic inflammatory state (Ogura et al., Immunity 29:628-36 (2008)). Antagonizing IL-17A can effectively alleviate rheumatoid arthritis symptoms. In a mouse model with collagen-induced arthritis, neutralizing IL-17A or its receptor thereof can resolve the symptoms of rheumatoid arthritis (Chao et al., Autoimmunity. 2011 May; 44 (3): 243-52); IL-17 deficiency can protect a host mouse from collagen-induced arthritis (Nakae et al., J Immunol, 171:6173-7 (2003)) while IL-17A overexpression can aggravate such conditions (Lubberts et al., Inflamm Res 51:102-4 (2002)).

Ankylosing spondylitis (AS) is a chronic autoimmune disease. The early pathological features of AS are acute or chronic inflammations at the bone attachment points of sacroiliac joints, tendons, and ligaments, which could develop to discitis and facet arthritis at a later stage; and there is a phenomenon of decreased bone density in all patients with AS. Studies have shown that both the number of Th17 cells secreting IL-17A in peripheral blood and the concentration of the IL-17A of patients with AS are significantly elevated than those of healthy people (Gracey et al., Arthritis Rheumatol. 68:679-89. (2016)). IL-17A can activate a variety of cells such as macrophages, dendritic cells, endothelial cells, fibroblasts, chondrocytes, and osteoblasts, which can produce a large number of inflammatory destructive factors (Ogura et al., Immunity 29:628-36 (2008)). In bone tissues, IL-17A induces osteoblasts to express receptor activator of nuclear factor-K B ligand (RANKL), activates osteoclasts, thus inducing bone resorption, cumulatively exacerbating bone loss, and causing bone destruction directly or indirectly (Gaffen, Curr Rheumatol Rep 11:365-370 (2009)). Among patients with AS, the anti-IL-17A monoclonal antibody Secukinumab has shown excellent efficacy, which can significantly reduce the symptoms and signs of ankylosing spondylitis (Baeten et al., N Engl J Med, 373:2534-48 (2015)). Based on these results, Secukinumab is approved by the FDA for the treatment of ankylosing spondylitis.

Systemic lupus erythematosus (SLE) is an autoimmune disease that affects multiple systems. Specifically, antibodies against autoantigens appear in patients' bodies, which attack various tissues or organs directly or indirectly, and the most commonly affected areas include skin, joints and kidneys. Studies have shown that IL-17A plays a role in SLE. The ratio of cells producing IL-17A in peripheral blood of patients with SLE is increased, and the level of IL-17A in serum of patients is abnormally high (Chen et al., J Clin Immunol, 30:221-5 (2010)). Peripheral blood mononuclear cells of patients with SLE accompanied by renal damage can produce more total IgG, anti-dsDNA IgG and IL-6 when cultured with IL-17, indicating that IL-17 can participate in B cells activation (Dong Et al., Chin Med J (Engl), 116: 543-8 (2003)). It has also been recently found that IL-17A can cooperate with BAFF (B-cell activating factor) to protect B cells from apoptosis, thereby increasing the number of cells producing autoantibodies (Onishi et al., Immunology 129:311-21 (2010)).

SUMMARY OF THE INVENTION

After intensive study and creative effort, the inventors used mammalian cell expression systems to express recombinant IL-17A (24-155) as an antigen to immunize mice, and obtained a large number of hybridoma cell samples by fusion of mouse spleen cells and myeloma cells. The inventors obtained the following two hybridoma cell lines separately by screening a large number of the samples:

hybridoma cell line LT006 (IL-17A-13E9), which was deposited at China Center for Type Culture Collection (CCTCC) on Sep. 12, 2017 with an accession number of CCTCC NO: C2017102;

and hybridoma cell line LT007 (IL-17A-2G2), which was deposited at China Center for Type Culture Collection (CCTCC) on Sep. 12, 2017 with an accession number of CCTCC NO: C2017165.

The inventors surprisingly found:

the hybridoma cell line LT006 may secrete and produce a specific monoclonal antibody (named as 13E9) that specifically binds to IL-17A, and the monoclonal antibody can block the binding of IL-17A to IL-17RA very effectively;

the hybridoma cell line LT007 may secrete and produce a specific monoclonal antibody (named as 2G2) that specifically binds to IL-17A, and the monoclonal antibody can block the binding of IL-17A to IL-17RA very effectively;

furthermore, the inventors creatively prepared anti-IL-17A humanized antibodies (named as 13E9 H1L1, 13E9 H2L2, 13E9 H3L2; and 2G2 H1L1, 2G2 H2L2, 2G2 H3L3, respectively), all of which may bind to human IL-17A effectively, block the binding of IL-17A to IL-17A receptors, and inhibit the activation of downstream signaling pathways of the IL-17A receptors; the antibody of the present invention has the potential to produce drugs for preventing and/or treating autoimmune diseases such as psoriasis, rheumatoid arthritis, psoriatic arthritis, ankylosing spondylitis, and systemic lupus erythematosus.

The following invention is thus provided:

one aspect of the present invention relates to a monoclonal antibody or an antigen binding fragment thereof, wherein, the heavy chain variable region (VH) of the monoclonal antibody comprises: HCDR1-HCDR3 with the amino acid sequences shown in SEQ ID NOs: 31-33 respectively, or HCDR1-HCDR3 with the amino acid sequences shown in SEQ ID NOs: 37-39 respectively; and the light chain variable region (VL) of the monoclonal antibody comprises: LCDR1-LCDR3 with the amino acid sequences shown in SEQ ID NOs: 34-36 respectively, or LCDR1-LCDR3 with the amino acid sequences shown in SEQ ID NOs: 40-42 respectively.

The variable regions of the light chain and the heavy chain determine the binding of the antigen; the variable region of each chain contains three hypervariable regions, namely complementarity determining regions (CDRs) (the CDRs of the heavy chain (H) include HCDR1, HCDR2, HCDR3, and the CDRs of the light chain (L) include LCDR1, LCDR2, LCDR3; defined by Kabat et al., see Sequences of Proteins of Immunological Interest, Fifth Edition (1991), Volumes 1-3, NIH Publication 91-3242, Bethesda Md).

The amino acid sequences of the CDR regions of the monoclonal antibody in (1) to (2) above are analyzed by technical means well known to those skilled in the art, for example, by a VBASE2 database:

the antibodies 13E9, 13E9 H1L1, 13E9 H2L2, and 13E9 H3L2 of the present invention have the same CDRs:

the amino acid sequences of the three CDR regions of the heavy chain variable region are as follows:

```
HCDR1:
                              (SEQ ID NO: 31)
SYSFTSDYA,

HCDR2:
                              (SEQ ID NO: 32)
ITYSGVT,
```

-continued

```
HCDR3:
                              (SEQ ID NO: 33)
ARADYDSYYTMDY;
``` and
the amino acid sequences of the three CDR regions of the
light chain variable region are as follows:

```
LCDR1:
                              (SEQ ID NO: 34)
QSLVHSNGNTY,

LCDR2:
                              (SEQ ID NO: 35)
KVS,

LCDR3:
                              (SEQ ID NO: 36)
SQSTHFWT.
```

The antibodies 2G2, 2G2 H1L1, 2G2 H2L2, and 2G2
H3L3 of the present invention have the same CDRs:
the amino acid sequences of the three CDR regions of the
heavy chain variable region are as follows:

```
HCDR1:
                              (SEQ ID NO: 37)
SEVFPIAD,

HCDR2:
                              (SEQ ID NO: 38)
ILPSFGRT,

HCDR3:
                              (SEQ ID NO: 39)
ARGNYGFAY;
``` and
the amino acid sequences of the three CDR regions of the
light chain variable region are as follows:

```
LCDR1:
                              (SEQ ID NO: 40)
QSLLNSDGKTY,

LCDR2:
                              (SEQ ID NO: 41)
LVS,

LCDR3:
                              (SEQ ID NO: 42)
WQGSHFPQT.
```

In one or more embodiments of the present invention, the
monoclonal antibody or the antigen binding fragment
thereof, wherein,
the heavy chain variable region (VH) of the monoclonal
antibody comprises HCDR1-HCDR3 with the amino
acid sequences shown in SEQ ID NOs: 31-33 respec-
tively, and
the light chain variable region (VL) of the monoclonal
antibody comprises LCDR1-LCDR3 with the amino
acid sequences shown in SEQ ID NOs: 34-36 respec-
tively.
In one or more embodiments of the present invention, the
monoclonal antibody or the antigen binding fragment
thereof, wherein,
the heavy chain variable region (VH) of the monoclonal
antibody comprises HCDR1-HCDR3 with the amino
acid sequences shown in SEQ ID NOs: 37-39 respec-
tively, and the light chain variable region (VL) of the monoclonal
antibody comprises LCDR1-LCDR3 with the amino
acid sequences shown in SEQ ID NOs: 40-42 respec-
tively.
In one or more embodiments of the present invention, the
monoclonal antibody or the antigen binding fragment
thereof, wherein,
the amino acid sequence of the heavy chain variable
region is selected from SEQ ID NO: 2, SEQ ID NO: 6,
SEQ ID NO: 10, SEQ ID NO: 14, SEQ ID NO: 16,
SEQ ID NO: 20, SEQ ID NO: 24, and SEQ ID NO: 28;
and
the amino acid sequence of the light chain variable region
is selected from SEQ ID NO: 4, SEQ ID NO: 8, SEQ
ID NO: 12, SEQ ID NO: 18, SEQ ID NO: 22, SEQ ID
NO: 26, and SEQ ID NO: 30.
In one or more embodiments of the present invention, the
monoclonal antibody or the antigen binding fragment
thereof, wherein,
the amino acid sequence of the heavy chain variable
region is selected from SEQ ID NO: 2, SEQ ID NO: 6,
SEQ ID NO: 10, and SEQ ID NO: 14, and the amino
acid sequence of the light chain variable region is
selected from SEQ ID NO: 4, SEQ ID NO: 8, and SEQ
ID NO: 12;
or
the amino acid sequence of the heavy chain variable
region is selected from SEQ ID NO: 16, SEQ ID NO:
20, SEQ ID NO: 24, and SEQ ID NO: 28, and the
amino acid sequence of the light chain variable region
is selected from SEQ ID NO: 18, SEQ ID NO: 22, SEQ
ID NO: 26, and SEQ ID NO: 30.
In one or more embodiments of the present invention, the
monoclonal antibody or the antigen binding fragment
thereof, wherein the heavy chain variable region and light
chain variable region are selected from any one of the
following (1) to (8):
(1) a heavy chain variable region comprising the amino
acid sequence shown in SEQ ID NO: 2, and
a light chain variable region comprising the amino acid
sequence shown in SEQ ID NO: 4;
(2) a heavy chain variable region comprising the amino
acid sequence shown in SEQ ID NO: 6, and
a light chain variable region comprising the amino acid
sequence shown in SEQ ID NO: 8;
(3) a heavy chain variable region comprising the amino
acid sequence shown in SEQ ID NO: 10, and
a light chain variable region comprising the amino acid
sequence shown in SEQ ID NO: 12;
(4) a heavy chain variable region comprising the amino
acid sequence shown in SEQ ID NO: 14, and
a light chain variable region comprising the amino acid
sequence shown in SEQ ID NO: 12;
(5) a heavy chain variable region comprising the amino
acid sequence shown in SEQ ID NO: 16, and
a light chain variable region comprising the amino acid
sequence shown in SEQ ID NO: 18;
(6) a heavy chain variable region comprising the amino
acid sequence shown in SEQ ID NO: 20, and
a light chain variable region comprising the amino acid
sequence shown in SEQ ID NO: 22;
(7) a heavy chain variable region comprising the amino
acid sequence shown in SEQ ID NO: 24, and
a light chain variable region comprising the amino acid
sequence shown in SEQ ID NO: 26; and
(8) a heavy chain variable region comprising the amino
acid sequence shown in SEQ ID NO: 28, and a light chain variable region comprising the amino acid sequence shown in SEQ ID NO: 30.

In one or more embodiments of the present invention, the monoclonal antibody or the antigen binding fragment thereof, wherein the monoclonal antibody or the antigen binding fragment thereof is selected from a Fab, a Fab', an F(ab')2, an Fd, an Fv, a dAb, a complementarity determining region fragment, a single chain antibody, a humanized antibody, a chimeric antibody and a diabody.

In one or more embodiments of the present invention, the monoclonal antibody or the antigen binding fragment thereof, wherein, the monoclonal antibody binds to IL-17A protein with an EC50 of less than about 100 nM, such as less than about 10 nM, 5 nM, 4 nM, 3 nM, 2.5 nM, 2 nM, or less; preferably, the EC50 is measured by a competitive ELISA method.

In some embodiments of the present invention, the monoclonal antibody or the antigen binding fragment thereof, wherein the monoclonal antibody binds to IL-17A protein with a KD of less than about 10-5 M, such as less than about 10-6 M, 10-7 M, 10-8 M, 10-9 M, 10-10 M, or less; preferably, the KD is measured by a Fortebio molecular interaction instrument.

In some embodiments of the present invention, the monoclonal antibody or the antigen binding fragment thereof, wherein the monoclonal antibody binds to IL-17A protein with an EC50 of less than about 100 nM, such as less than about 10 nM, 1 nM, 0.9 nM, 0.8 nM, 0.7 nM, 0.6 nM, 0.5 nM, 0.4 nM, 0.3 nM, 0.2 nM, 0.1 nM, or less; in particular, the EC50 is measured by an indirect ELISA method.

In one or more embodiments of the present invention, the monoclonal antibody comprises non-CDR regions, and the non-CDR regions are from species other than murine, such as from a human antibody.

In some embodiments of the present invention, the constant region of the immunoglobulin is humanized, for example, the heavy chain constant regions use Ig gamma-1 chain C region, ACCESSION: P01857; and the light chain constant regions use Ig kappa chain C region, ACCESSION: P01834.

In one or more embodiments of the present invention, the monoclonal antibody or the antigen binding fragment thereof, wherein:

the monoclonal antibody is produced by the hybridoma cell line LT006, which was deposited at China Center for Type Culture Collection (CCTCC) with an accession number of CCTCC NO: C2017102; or the monoclonal antibody is produced by the hybridoma cell line LT007, which was deposited at China Center for Type Culture Collection (CCTCC) with an accession number of CCTCC NO: C2017165.

In one or more embodiments of the present invention, the monoclonal antibody or the antigen binding fragment thereof is used to prevent and/or treat tumors or autoimmune diseases, or to diagnose autoimmune diseases; preferably, the autoimmune disease is selected from psoriasis, rheumatoid arthritis, psoriatic arthritis, ankylosing spondylitis, and systemic lupus erythematosus; preferably, the psoriasis is moderate to severe plaque psoriasis.

In one or more embodiments of the present invention, the monoclonal antibody or an antigen binding fragment thereof is used for:

blocking the binding of IL-17A to IL-17RA, regulating (e.g., down-regulating) IL-17A activity or level, or inhibiting IL-6 expression in cells.

Another aspect of the present invention relates to an isolated nucleic acid molecule comprising nucleotide sequences encoding the heavy chain variable region and light chain variable region of any one of the monoclonal antibodies described in the present invention.

In one or more embodiments of the present invention, the isolated nucleic acid molecule comprises nucleotide sequences selected from any of the following (1) to (8):

(1) SEQ ID NO: 1, SEQ ID NO: 3;

(2) SEQ ID NO: 5, SEQ ID NO: 7;

(3) SEQ ID NO: 9, SEQ ID NO: 11;

(4) SEQ ID NO: 13, SEQ ID NO: 11;

(5) SEQ ID NO: 15, SEQ ID NO: 17;

(6) SEQ ID NO: 19, SEQ ID NO: 21;

(7) SEQ ID NO: 23, SEQ ID NO: 25; and (8) SEQ ID NO: 27, SEQ ID NO: 29.

Another aspect of the present invention relates to a recombinant vector comprising the isolated nucleic acid molecule of the present invention. Preferably, the recombinant vector is a recombinant expression vector, such as a recombinant prokaryotic expression vector or a recombinant eukaryotic expression vector.

Another aspect of the present invention relates to a host cell comprising the recombinant vector of the present invention.

Another aspect of the present invention relates to a method for preparing any one of the monoclonal antibodies or the antigen binding fragments thereof described in the present invention, comprising the steps of culturing the host cell in the present invention under appropriate conditions and isolating the monoclonal antibody or the antigen binding fragment thereof from the cell cultures.

Another aspect of the present invention relates to a hybridoma cell line selected from:

the hybridoma cell line LT006, which was deposited at China Center for Type Culture Collection (CCTCC) with an accession number of CCTCC NO: C2017102; and the hybridoma cell line LT007, which was deposited at China Center for Type Culture Collection (CCTCC) with an accession number of CCTCC NO: C2017165.

Another aspect of the present invention relates to a conjugate comprising a monoclonal antibody or an antigen binding fragment thereof and a conjugated portion, wherein the monoclonal antibody is any one of the monoclonal antibodies or the antigen binding fragments thereof described in the present invention, the conjugated portion is a detectable label; preferably, the detectable label is a radioactive isotope, a luminescent substance such as a fluorescent substance, a colored substance, or an enzyme.

Another aspect of the present invention relates to a kit comprising any one of the monoclonal antibodies or the antigen binding fragments thereof described in the present invention or comprising the conjugate of the present invention;

preferably, the kit further comprises a second antibody which specifically recognizes the monoclonal antibody or the antigen binding fragment thereof; optionally, the second antibody further comprises a detectable label; preferably, the detectable label is a radioactive isotope, a luminescent substance such as a fluorescent substance, a colored substance, or an enzyme.

Another aspect of the present invention relates to use of any one of the monoclonal antibodies or the antigen binding fragments thereof described in the present invention or the conjugate of the present invention in the preparation of a kit for qualitative or quantitative detection for IL-17A. The qualitative detection refers to detecting the presence of IL-17A in the sample to be tested, and the quantitative detection refers to detecting the concentration or content of IL-17A in the sample to be tested.

Another aspect of the present invention relates to a pharmaceutical composition comprising any one of the monoclonal antibodies or the antigen binding fragments thereof described in the present invention or the conjugate of the present invention; optionally, the pharmaceutical composition further comprises pharmaceutically acceptable carriers or excipients.

Another aspect of the present invention relates to use of any one of the monoclonal antibodies or the antigen binding fragments thereof described in the present invention or the conjugate of the present invention in the preparation of a drug for preventing and/or treating tumors or autoimmune diseases, or use in the preparation of a drug for diagnosing autoimmune diseases; preferably, the autoimmune disease is selected from psoriasis, rheumatoid arthritis, psoriatic arthritis, ankylosing spondylitis, and systemic lupus erythematosus; preferably, the psoriasis is moderate to severe plaque psoriasis.

In particular, the inventors found from animal experiments (Example 11) that 13E9H3L2 can effectively inhibit the increase in the epidermal thickness of a C57BL/6 mouse model with psoriasis, which is shown as the antibody drug 13E9H3L2 can significantly inhibit the increase of epidermal thickness of the mouse caused by IL-17A and subcutaneous injection, having an efficacy equivalent to the marketed monoclonal antibody drug Secukinumab for the same target.

In some embodiments of the present invention, the autoimmune diseases (e.g., psoriasis such as moderate to severe plaque psoriasis, rheumatoid arthritis, psoriatic arthritis, ankylosing spondylitis or systemic lupus erythematosus) are caused by an elevated IL-17A expression level. The elevated expression level described here refers to the expression level higher than that of healthy people and has reached a pathogenic level.

Another aspect of the present invention relates to use of any one of the monoclonal antibodies or the antigen binding fragments thereof described in the present invention or the conjugate of the present invention in the preparation of the following drugs:

drugs blocking the binding of IL-17A to IL-17RA,
    drugs regulating (e.g., down-regulating) IL-17A activity or level, or
    drugs inhibiting IL-6 expression in cells.

Another aspect of the present invention relates to an in vivo or in vitro method comprising the step of administering to a cell or a subject in need an effective amount of any one of the monoclonal antibodies or the antigen binding fragments thereof described in the present invention or the conjugate of the present invention, and the method is selected from the following:

methods for blocking the binding of IL-17A to IL-17RA,
    methods for regulating (e.g., down-regulating) IL-17A activity or level, or
    methods for inhibiting IL-6 expression in fibroblasts.

In a specific embodiment of the present invention, the in vitro method is non-therapeutic and/or non-diagnostic.

Interleukin 6 (abbreviated as IL-6 or IL 6) can be produced by fibroblasts, monocytes/macrophages, T lymphocytes, B lymphocytes, epithelial cells, keratinocytes, and various tumor cells. Interleukin 6 is an important factor regulating immune response, and IL-6 and IL-1 can synergistically promote T cell proliferation, stimulate B cell differentiation, and participate in the body's inflammatory responses (Schoenborn et al. Advances in Immunology 96:41-101 (2007)). The in vitro experiment (Example 10) of the present invention shows that the anti-IL-17A antibody can significantly reduce the secretion of IL-6 and inhibit IL-6-mediated immune response.

Another aspect of the present invention relates to a method for treating and/or preventing tumors or autoimmune diseases, and the method comprises the step of administering to a subject in need an effective amount of any one of the monoclonal antibodies or the antigen binding fragments thereof described in the present invention or the conjugate of the present invention; preferably, the autoimmune disease is selected from psoriasis, rheumatoid arthritis, psoriatic arthritis, ankylosing spondylitis, and systemic lupus erythematosus; preferably, the psoriasis is moderate to severe plaque psoriasis.

Another aspect of the present invention relates to a method for diagnosing autoimmune diseases, and the method comprises the step of applying a sample to be tested (such as a tissue sample, a cell sample, or a blood sample) or administering to a subject in need an effective amount of any one of the monoclonal antibodies or the antigen binding fragments thereof described in the present invention or the conjugate of the present invention; preferably, the autoimmune disease is selected from psoriasis, rheumatoid arthritis, psoriatic arthritis, ankylosing spondylitis, and systemic lupus erythematosus; preferably, the psoriasis is moderate to severe plaque psoriasis.

In some embodiments of the present invention, considering that autoimmune diseases (e.g., psoriasis, such as moderate to severe plaque psoriasis, rheumatoid arthritis, psoriatic arthritis, ankylosing spondylitis or systemic lupus erythematosus) are caused by an elevated IL-17A expression level, thus the diagnosis can be performed by detecting the IL-17A expression level using any one of the monoclonal antibodies or the antigen binding fragments thereof described in the present invention or the conjugate of the present invention. If the IL-17A expression level is higher than that of healthy people and has reached the pathogenic level, the diagnosis is a positive result; otherwise, the diagnosis is a negative result.

In the present invention, unless otherwise defined, the scientific and technical terms used herein have the meanings generally understood by those skilled in the art. In addition, the laboratory operations of cell culture, molecular genetics, nucleic acid chemistry and immunology used herein are the routine operations widely used in the corresponding fields. Meanwhile, in order to better understand the present invention, the definitions and explanations of the relevant terms are provided below.

As used herein, when the amino acid sequence of the IL-17A (interleukin-17A) protein is mentioned, it includes the full length of the IL-17A protein; also a fusion protein of IL-17A, such as a fragment fused to a mouse or human IgG Fc protein fragment (mFc or hFc). However, those skilled in the art will understand that in the amino acid sequence of the IL-17A protein, mutations or variations (including but not limited to, substitutions, deletions and/or additions) can be naturally generated or artificially introduced without affecting biological functions thereof. Therefore, in the present invention, the term "IL-17A protein" should include all such sequences, including their natural or artificial variants. In addition, when the sequence fragment of the IL-17A protein is described, the IL-17A protein also includes the corresponding sequence fragments in natural or artificial variants thereof.

The full-length sequence (155aa) of IL-17A is as follows, wherein the signal peptide sequence (23aa) is underlined.

```
                                       (SEQ ID NO: 43)
MTPGKTSLVSLLLLLSLEAIVKAGITIPRNPGCPNSEDKNFPRTVMVNL

NIHNRNTNTNPKRSSDYYNRSTSPWNLHRNEDPERYPSVIWEAKCRHLG

CINADGNVDYHMNSVPIQQEILVLRREPPHCPNSFRLEKILVSVGCTCV

TPIVHHVA
```

As used herein, unless otherwise defined, the IL-17R is IL-17RA; specific protein sequence thereof is a sequence known in the prior art, and reference may be made to the sequence disclosed in the existing literature or GenBank. For example, IL-17RA (CD217, NCBI Gene ID: NP_055154.3).

As used herein, the term EC50 refers to the concentration for 50% of maximal effect, i.e. the concentration that can cause 50% of the maximal effect.

As used herein, the term "antibody" refers to an immunoglobulin molecule that generally consists of two pairs of polypeptide chains (each pair with one "light" (L) chain and one "heavy" (H) chain). In a general sense, the heavy chain can be interpreted as a polypeptide chain with a larger molecular weight in an antibody, and the light chain refers to a polypeptide chain with a smaller molecular weight in an antibody. Light chains are classified as k and A light chains. Heavy chains are generally classified as u, 8, y, a, or ¿, and isotypes of antibodies are defined as IgM, IgD, IgG, IgA, and IgE, respectively. In light chains and heavy chains, the variable region and constant region are linked by a "J" region of about 12 or more amino acids, and the heavy chain also comprises a "D" region of about 3 or more amino acids. Each heavy chain consists of a heavy chain variable region (VH) and a heavy chain constant region (CH). The heavy chain constant region consists of 3 domains (CH1, CH2 and CH3). Each light chain consists of a light chain variable region (VL) and a light chain constant region (CL). The light chain constant region consists of one domain CL. The constant region of the antibody can mediate the binding of immunoglobulins to host tissues or factors, including the binding of various cells of the immune system (e.g., effector cells) to the first component (C1q) of classical complement system. The VH and VL regions can be further subdivided into highly variable regions (called complementarity determining regions (CDRs)), and between which conservative regions called framework regions (FRs) are distributed. Each VH and VL consists of 3 CDRs and 4 FRs arranged from amino terminus to carboxyl terminus in the following order: FR1, CDR1, FR2, CDR2, FR3, CDR3, FR4. The variable regions (VH and VL) of each heavy chain/light chain pair form an antibody binding site, respectively. The assignment of amino acids to each region or domain follows the definition of Kabat Sequences of Proteins of Immunological Interest (National Institutes of Health, Bethesda, Md. (1987 and 1991)), or Chothia & Lesk (1987) J. Mol. Biol. 196:901-917; Chothia et al. (1989) Nature 342:878-883. In particular, the heavy chain may also comprise more than 3 CDRs, such as 6, 9, or 12. For example, in the bispecific antibody of the present invention, the heavy chain may be a ScFv with the C-terminus of the heavy chain of IgG antibody linked to another antibody, and in this case, the heavy chain comprises 9 CDRs. The term "antibody" is not restricted by any specific method for producing antibody. For example, the antibody includes, in particular, a recombinant antibody, a monoclonal antibody or a polyclonal antibody. Antibodies can be different isotypes, such as antibodies IgG (e.g., subtypes IgG1, IgG2, IgG3 or IgG4), IgA1, IgA2, IgD, IgE or IgM.

As used herein, the term "antigen binding fragment" refers to the polypeptide comprising the fragment of a full-length antibody, which maintains the ability to specifically bind to the same antigen to which the full-length antibody binds, and/or competing with the full-length antibody for the specific binding to antigen, which is also known as the "antigen binding portion". See generally, Fundamental Immunology, Ch. 7 (Paul, W., ed., 2nd edition, Raven Press, N.Y. (1989), which is incorporated herein by reference in its entirety for all purposes. Antigen binding fragment of the antibody can be produced by recombinant DNA technology or by enzymatic or chemical cleavage of intact antibodies. In some cases, the antigen binding fragment includes a Fab, a Fab', an F(ab') 2, an Fd, an Fv, a dAb, a complementarity determining region (CDR) fragment, a single chain antibody fragment (e.g., scFv), a chimeric antibody, a diabody and such polypeptide, which comprises at least a portion of the antibody sufficient to impart specific antigen binding ability to a polypeptide.

As used herein, the term "Fd fragment" refers to an antibody fragment consisting of VH and CH1 domains; the term "Fv fragment" refers to an antibody fragment consisting of the VL and VH domains of a single arm of an antibody; the term "dAb fragment" refers to an antibody fragment consisting of a VH domain (Ward et al., Nature 341:544 546 (1989)); the term "Fab fragment" refers to an antibody fragment consisting of VL, VH, CL, and CH1 domains; and the term "F(ab')2 fragment" refers to an antibody fragment comprising two Fab fragments linked by the disulfide bridge on a hinge region.

In some cases, the antigen binding fragment of the antibody is a single chain antibody (e.g., scFv) in which the VL and VH domains are paired to form a monovalent molecule via a linker that enables them to produce a single polypeptide chain (see, e.g., Bird et al., Science 242:423 426 (1988) and Huston et al., Proc. Natl. Acad. Sci. USA 85:5879 5883 (1988)). Such scFv molecules may have a general structure: NH2-VL-linker-VH-COOH or NH2-VH-linker-VL-COOH. An appropriate prior art linker consists of a repeating GGGGS (SEQ ID NO: 44) amino acid sequence or a variant thereof. For example, a linker having the amino acid sequence (GGGGS) 4 (SEQ ID NO: 45) can be used, but variants thereof can also be used (Holliger et al. (1993), Proc. Natl. Acad. Sci. USA 90:6444-6448). Other linkers that can be used in the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol.

In some cases, the antigen binding fragment of the antibody is a diabody, that is, a bivalent antibody, in which the VH and VL domains are expressed on a single polypeptide chain. However, the linker used is too short to allow the pairing of the two domains on the same chain, thereby the domains are forced to pair with the complementary domains on the other chain and two antigen binding sites are generated (see, e.g., Holliger P. et al., Proc. Natl. Acad. Sci. USA 90:6444 6448 (1993), and Poljak R J et al., Structure 2:1121 1123 (1994)).

Antigen binding fragments (e.g., the above mentioned antibody fragments) of antibodies can be obtained from given antibodies by using conventional techniques known to those skilled in the art (e.g., recombinant DNA technology or enzymatic or chemical cleavage), and the antigen binding fragments of the antibodies are screened for specificity in the same way as for intact antibodies.

As used herein, unless otherwise clearly defined in the context, when referring to the term "antibody", it includes not only intact antibodies but also antigen binding fragments of antibodies.

As used herein, the terms "mAb" and "monoclonal antibody" refer to an antibody or a fragment of an antibody that is derived from a group of highly homologous antibodies, i.e. from a group of identical antibody molecules, except for natural mutations that may occur spontaneously. The monoclonal antibody has a high specificity for a single epitope on an antigen. The Polyclonal antibody, relative to the monoclonal antibody, generally comprises at least two or more different antibodies which generally recognize different epitopes on an antigen. Monoclonal antibodies can generally be obtained by hybridoma technology first reported by Kohler et al. (Nature, 256:495, 1975), but can also be obtained by recombinant DNA technology (for example, see U.S. Pat. No. 4,816,567).

As used herein, the term "chimeric antibody" refers to an antibody of which a part of the light or/and heavy chains is derived from an antibody (which may be derived from a specific species or belong to a specific antibody class or subclass), and the other part of the light or/and heavy chains are derived from another antibody (which may be derived from the same or different species or belong to the same or different antibody class or subclass). But in any case, it retains the binding activity to the target antigen (U.S. Pat. No. 4,816,567 to Cabilly et al.; Morrison et al., Proc. Natl. Acad. Sci. USA, 81:6851 6855 (1984)).

As used herein, the term "humanized antibody" refers to an antibody or antibody fragment obtained when all or a part of CDR regions of a human immunoglobulin (receptor antibody) are replaced by the CDR regions of a non-human antibody (donor antibody), wherein the donor antibody may be a non-human (e.g., mouse, rat or rabbit) antibody having expected specificity, affinity or reactivity. In addition, some amino acid residues in the framework regions (FRs) of the receptor antibody can also be replaced by the amino acid residues of corresponding non-human antibodies or by the amino acid residues of other antibodies to further improve or optimize the performance of the antibody. For more details on humanized antibodies, see, for example, Jones et al., Nature, 321:522 525 (1986); Reichmann et al., Nature, 332:323 329 (1988); Presta, Curr. Op Struct. Biol., 2:593 596 (1992); and Clark, Immunol. Today 21:397 402 (2000).

As used herein, the term "epitope" refers to a site on the antigen that an immunoglobulin or antibody specifically binds to. "Epitope" is also called in the art as an "antigenic determinant". The epitope or antigenic determinant generally consists of chemically active surface groups of a molecule such as amino acids or carbohydrates or sugar side chains, and usually has specific three-dimensional structural characteristics and specific charge characteristics. For example, the epitope generally includes at least 3, 4, 5, 6, 7, 8, 9, 10, 11, 12, 13, 14, or 15 consecutive or non-consecutive amino acids in a unique spatial conformation, which can be "linear" or "conformational". See, for example, Epitope Mapping Protocols in Methods in Molecular Biology, Vol. 66, G. E. Morris, Ed. (1996). In a linear epitope, all interacting points between a protein and an interacting molecule (e.g., an antibody) exist linearly along the primary amino acid sequence of the protein. In a conformational epitope, the interacting points exist across the protein amino acid residues that are separated from each other.

As used herein, the term "isolated" refers to obtained by artificial means from natural state. If a certain "isolated" substance or component appears in nature, it may be due to the change in its natural environment, or it is isolated from the natural environment, or both. For example, a certain non-isolated polynucleotide or polypeptide naturally exists in a certain living animal, and the same polynucleotide or polypeptide with a high purity isolated from such a natural state is called isolated polynucleotide or polypeptide. The term "isolated" does not exclude the existence of artificial or synthetic substances or other impurities that do not affect the activity of the substance.

As used herein, the term "E. coli expression system" refers to an expression system consisting of E. coli (strain) and a vector, wherein the E. coli (strain) is derived from a commercially available strain, such as but not limited to GI698, ER2566, BL21 (DE3), B834 (DE3), and BLR (DE3).

As used herein, the term "vector" refers to a nucleic acid vehicle into which a polynucleotide can be inserted. When the vector allows for the expression of the protein encoded by the inserted polynucleotide, the vector is called an expression vector. A vector can be introduced into a host cell by transformation, transduction, or transfection so that the genetic substance elements carried by the vector can be expressed in the host cell. Vectors are well known to those skilled in the art, including, but not limited to: plasmids; phagemids; cosmids; artificial chromosomes, such as yeast artificial chromosomes (YAC), bacterial artificial chromosomes (BAC) or P1-derived artificial chromosomes (PAC); phages such as lambda phages or M13 phages, and animal viruses, etc. Animal viruses that can be used as vectors include, but are not limited to, retroviruses (including lentiviruses), adenoviruses, adeno-associated viruses, herpes viruses (such as herpes simplex virus), poxviruses, baculoviruses, papillomaviruses, and papovaviruses (such as SV40). A vector can contain a variety of elements that control expression, including, but not limited to, promoter sequences, transcription initiation sequences, enhancer sequences, selection elements, and reporter genes. In addition, the vector may further contain a replication initiation site.

As used herein, the term "host cell" refers to cells that can be used to introduce vectors, including, but not limited to, prokaryotic cells such as E. coli or Bacillus subtilis, fungal cells such as yeast cells or aspergillus, insect cells such as S2 drosophila cells or Sf9, or animal cells such as fibroblast, CHO cells, COS cells, NSO cells, HeLa cells, BHK cells, HEK 293 cells, or human cells.

As used herein, the term "KD" refers to a dissociation equilibrium constant for a specific antibody-antigen interaction, which is used to describe the binding affinity between the antibody and the antigen. The smaller the equilibrium dissociation constant, the tighter the antibody-antigen binding, and the higher the affinity between the antibody and the antigen. Generally, antibodies bind to antigens with a dissociation equilibrium constant (KD) of less than about 10-5 M, such as less than about 10-6 M, 10-7 M, 10-8 M, 10-9 M, 10-10 M, or less, and the dissociation equilibrium constant can be measured by, for example, using a Fortebio molecular interaction instrument.

As used herein, the terms "monoclonal antibody" and "mAb" have the same meaning and can be used interchangeably; the terms "polyclonal antibody" and "PcAb" have the same meaning and can be used interchangeably; the terms "polypeptide" and "protein" have the same meaning and can be used interchangeably. And in the present invention, amino acids are generally represented by single-letter and three-letter abbreviations known in the art. For example, alanine can be represented by A or Ala.

As used herein, the terms "hybridoma" and "hybridoma cell line" can be used interchangeably, and when referring to the terms "hybridoma" and "hybridoma cell line", they also include subclones and progeny cells of the hybridoma. For example, when referring to hybridoma cell line LT006 or LT007, it also refers to subclones and progeny cells of the hybridoma cell line LT006 or LT007.

As used herein, the term "pharmaceutically acceptable carrier and/or excipient" refers to a carrier and/or excipient that is pharmacologically and/or physiologically compatible with the subject and the active ingredient, which is well known in the art (see, e.g., Remington's Pharmaceutical Sciences. Edited by Gennaro AR, 19th ed. Pennsylvania: Mack Publishing Company, 1995), and includes but is not limited to pH regulators, surfactants, adjuvants, and ionic strength enhancers. For example, the pH regulators include, but are not limited to, phosphate buffer; the surfactants include, but are not limited to, cationic, anionic, or non-ionic surfactants, such as TWEEN®-80; and the ionic strength enhancers include, but are not limited to, sodium chloride.

As used herein, the term "adjuvant" refers to a non-specific immune enhancer, which can enhance the immune response of the body to antigens or change the type of immune response when delivered into the body together with the antigens or delivered into the body in advance. There are various adjuvants, including, but not limited to, aluminum adjuvant (e.g., aluminum hydroxide), Freund's adjuvant (e.g., complete Freund's adjuvant and incomplete Freund's adjuvant), *Corynebacterium parvum*, lipopolysaccharide, cytokine, etc. The Freund's adjuvant is the most commonly used adjuvant in animal experiments. The aluminum hydroxide adjuvant is used more in clinical trials.

As used herein, the term "effective amount" refers to an amount sufficient to obtain or at least partially obtain desired effect. For example, the effective amount for preventing diseases (e.g., diseases related to IL-17A binding to IL-17A receptor or excessive IL-17A activity, such as autoimmune diseases) is an amount sufficient to prevent, stop, or delay the onset of diseases (e.g., diseases related to IL-17A binding to IL-17A receptor or excessive IL-17A activity, such as autoimmune diseases); a therapeutically effective amount is an amount sufficient to cure or at least partially stop a disease and its complications in patients who have already had the disease. It is well within the ability of those skilled in the art to determine such an effective amount. For example, the amount effective for therapeutic use will depend on the severity of the disease to be treated, the overall state of the patient's own immune system, the general condition of the patient such as age, weight and gender, the manner of drug administration, and other treatments administered concurrently, etc.

The Beneficial Effects of The Invention

The present invention achieves at least one of the following technical effects:

(1) the monoclonal antibodies of the present invention such as 13E9 H1L1, 13E9 H2L2, 13E9 H3L2, and 2G2 H1L1, 2G2 H2L2, 2G2 H3L3 all can specifically bind to IL-17A very well, and can effectively block the binding of IL-17A to the IL-17A ligand and specifically reduce secretion of IL-6 in the IL-17A-mediated fibroblasts;

(2) the monoclonal antibodies of the present invention, especially 13E9 H2L2, have the same effect as the marketed drug Secukinumab for the same target in inhibiting the secretion of IL-6;

(3) the monoclonal antibodies of the present invention have the potential to be applied in the treatment and/or prevention of anti-autoimmune diseases such as psoriasis, rheumatoid arthritis, psoriatic arthritis, ankylosing spondylitis or systemic lupus erythematosus.

Figure 1:
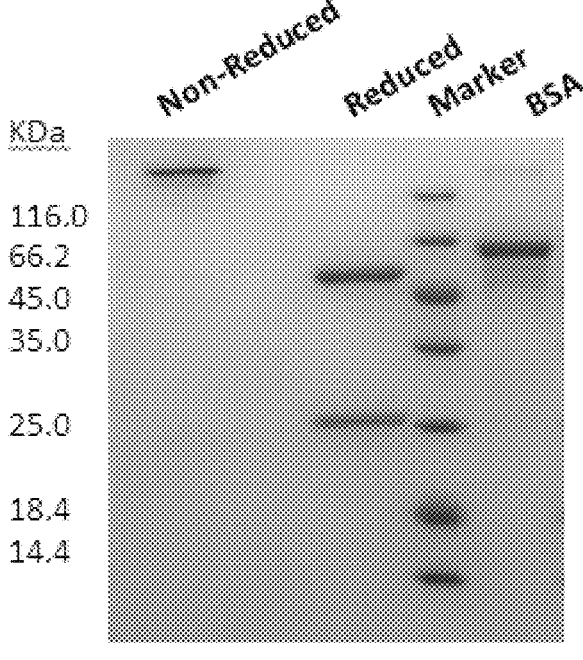
FIG. 1: SDS-PAGE detection results of the monoclonal murine antibody 13E9. The samples of the four lanes from left to right and their respective loading amounts are: antibody in non-reducing protein electrophoresis loading buffer, 1 μg; antibody in reducing protein electrophoresis loading buffer, 1 μg; Marker, 5 μL; BSA, 1 μg.

Notes on the preservation of biological materials:

hybridoma cell line LT006 (IL17A-13E9), which was deposited at China Center for Type Culture Collection (CCTCC) on Sep. 12, 2017 with an accession number of CCTCC NO: C2017102, at Wuhan University, Wuhan, China, 430072. hybridoma cell line LT007 (IL17A-2G2), which was deposited at China Center for Type Culture Collection (CCTCC) on Sep. 12, 2017 with an accession number of CCTCC NO: C2017165, at Wuhan University, Wuhan, China, 430072.

DETAILED DESCRIPTION

The embodiments of the present invention will be described in detail below with reference to the examples. Those skilled in the art will understand that the following examples are only used to illustrate the present invention, and should not be regarded as limiting the scope of the present invention. An example is performed according to the technologies or conditions described in the literature in the art (e.g., see, *Guide to Molecular Cloning Experiments*, authored by J. Sambrook et al., and translated by Huang Peitang et al., third edition, Science Press) or according to the product manual if specific technologies or conditions are not specified therein. Reagents or instruments used are all commercially available conventional products if the manufacturers thereof are not specified.

In the following examples, the BALB/C mice used were purchased from Guangdong Medical Laboratory Animal Center; the C57BL/6 mice used were from Nanjing Galaxy Biopharma Co., Ltd.; the MRC5 cells used were from Shanghai Fudan IBS Cell Center; the monoclonal antibody Secukinumab (Cosentyx®) used was purchased from Novartis Corporation.

Example 1: Preparation of anti-IL-17A antibodies 13E9 and 2G2

1. Preparation of the Hybridoma Cell Lines LT006 and LT007

Antigen IL17A (24-155)-his used to generate the anti-IL-17A antibody is the fusion protein of human IL-17A (Gen- Bank ID: Q16552) mature peptide and the His tag. Spleen cells from the immunized BALB/C mice (purchased from Guangdong Medical Laboratory Animal Center) and mouse myeloma cells were fused into hybridoma cells, and established methods (e.g., "Monoclonal Antibody Production", in Basic Methods in Antibody Production and Characterization, Eds. G. C. Howard and D. R. Bethell, Boca Raton: CRC Press, 2000) were referred to for specific operations.

The fusion protein IL17A-His was enzyme-digested with TEV protease and purified by column to obtain IL-17A (24-155) protein. Indirect ELISA screening was performed in coated microplates with the IL-17A (24-155) protein as the antigen to obtain hybridoma cells that secreted new antibodies specifically bound to IL-17A (24-155).

Hybridoma cells obtained by indirect ELISA screening were screened by competitive ELISA to obtain hybridoma cell lines capable of secreting a monoclonal antibody that competed with the receptor IL-17RA (CD217, NCBI Gene ID: NP_055154.3) for binding to IL-17A, and two stable hybridoma cell lines were obtained by limited dilution.

Hybridoma cell line LT006 (IL17A-13E9) was deposited at China Center for Type Culture Collection (CCTCC) on Saturday, Sep. 12, 2015 with an accession number of CCTCC NO: C2017102, at Wuhan University, Wuhan, China, 430072. The monoclonal antibody secreted by hybridoma cell line LT006 was named as 13E9.

Hybridoma cell line LT007 (IL17A-2G2) was deposited at China Center for Type Culture Collection (CCTCC) on Sep. 12, 2017 with an accession number of CCTCC NO: C2017165, at Wuhan University, Wuhan, China, 430072. The monoclonal antibody secreted by hybridoma cell line LT007 was named as 2G2.

2. Preparation of Anti-IL-17A Antibody 13E9

The LT006 cell line prepared above was cultured ($1 \times 10^5$ cells per well) with hybridoma serum-free medium (containing 1% Penicillin-Streptomycin and 4% Glutamax, cultured in a cell incubator at 37° C. with 5% $CO_2$), and the cell culture supernatant was collected when the survival rate was around 20% after 7 days of culturing, which was then subjected to high-speed centrifugation, vacuum filtration through a microporous membrane, and purification through a HiTrap protein A HP column to obtain antibody 13E9. The purified 13E9 samples were detected by SDS-PAGE electrophoresis, and the results are shown in FIG. 1.

3. Preparation of Anti-IL-17A Antibody 2G2

Figure 2:
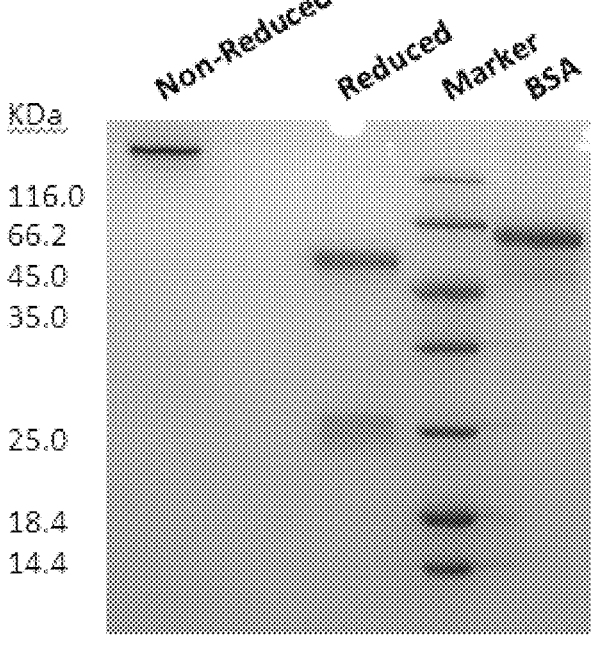
FIG. 2: SDS-PAGE detection results of the monoclonal murine antibody 2G2. The samples of the four lanes from left to right and their respective loading amounts are: antibody in non-reducing protein electrophoresis loading buffer, 1 μg; antibody in reducing protein electrophoresis loading buffer, 1 μg; Marker, 5 μL; BSA, 1 μg.

The LT007 cell line prepared above was cultured ($1 \times 10^5$ cells per well) with hybridoma serum-free medium (containing 1% Penicillin-Streptomycin and 4% Glutamax, cultured in a cell incubator at 37° C. with 5% $CO_2$), and the cell culture supernatant was collected when the survival rate was around 20% after 7 days of culturing, which was then subjected to high-speed centrifugation, vacuum filtration through a microporous membrane, and purification through a HiTrap protein A HP column to obtain antibody 2G2. The purified 2G2 samples were detected by SDS-PAGE electrophoresis, and the results are shown in FIG. 2.

Example 2: Sequence Analysis of Antibody 13E9

LT006 cells were cultured according to the method in step 2 of Example 1.

Using the cell/bacterial total RNA extraction kit (Tiangen, article number DP430), mRNA was extracted from the cultured LT006 cells according to the method in the kit manual.

cDNA was synthesized according to the kit manual of the Invitrogen SuperScript® III First-Strand Synthesis System for RT-PCR, and amplified by PCR.

The PCR-amplified products were directly TA cloned, and the kit manual of the pEASY-T1 Cloning Kit (Transgen CT101) was referred to for specific operations.

The TA-cloned products were directly sequenced, and the sequencing results are as follows:

nucleotide sequence of the heavy chain variable region: (360 bp)

(SEQ ID NO: 1)

GAAGTAAAGCTGCAGGAGTCGGGACCTGGCCTGGTGAAACCTTCTCAGT

CTCTGTCCCTCACCTGCACTGTCACTAGCTACTCATTCACCAGTGATTA

TGCCTGGAGCTGGATCCGGCAGTTTCCAGGAATCAAACTGGAGTGGATG

GGCTACATAACCTACAGTGGTGTCACTAGCTACAACCCCTCTCTCAAAA

GTCGAATCTCTATCACTCGAGACACATCCAAGAACCAGTTCTTCCTACA

GTTGAATTCTGTGACTACTGAGGACACGGCCACATATTACTGTGCAAGG

GCAGACTATGATAGCTACTATACTATGGACTACTGGGGTCAAGGAACCT

CAGTCACCGTCTCCTCA its encoded amino acid sequence: (120 aa)

(SEQ ID NO: 2)

EVKLQESGPGLVKPSQSLSLTCTVT<u>SYSFTSDYAWS</u>WIRQFPGIKLEWM

GY<u>ITYSGVTSYNPSLKSR</u>ISITRDTSKNQFFLQLNSVTTEDTATYYCAR

<u>ADYDSYYTMDY</u>WGQGTSVTVSS nucleotide sequence of the light chain variable region: (333 bp)

(SEQ ID NO: 3)

GACATCCAGCTGACTCAGTCTCCACTCTCCCTGCCTGTCAGTCTTGGAG

ATCAAGCCTCCATCTCTTGCAGATCTAGTCAGAGCCTTGTACACAGTAA

TGGAAACACCTATTTACATTGGTACCTGCAGAAGCCAGGCCAGTCTCCA

AGGCTCCTGATCTACAAAGTTTCCAACCGATTTTCTGGGGTCCCAGACA

GGTTCAGTGGCAGTGGATCAGGGACAGATTTCACACTCAAGATCAGCAG

AGTGGAGGCTGAGGATCTGGGAGTTTATTTCTGCTCTCAAAGTACACAT

TTTTGGACGTTCGGTGGAGGCACCAAGCTGGAAATAAAA its encoded amino acid sequence: (111 aa)

(SEQ ID NO: 4)

DIQLTQSPLSLPVSLGDQASISCRSS<u>QSLVHSNGNTYLH</u>WYLQKPGQSP

RLLIYK<u>VSNRFS</u>GVPDRFSGSGSGTDFTLKISRVEAEDLGVYFC<u>SQSTH</u>

<u>FWT</u>FGGGTKLEIK

The underlined regions are the CDR regions.

Example 3: Design, Preparation and Detection of Anti-IL-17A Humanized Antibodies 13E9 H1L1, 13E9 H2L2 and 13E9 H3L2

1. Design of the light chain and heavy chain sequences of anti-IL-17A humanized antibodies 13E9 H1L1, 13E9 H2L2 and 13E9 H3L2

Based on the three-dimensional crystal structure of the IL-17A protein (EMBO J. (2001) 20 p: 5332-41) and the sequence of the antibody 13E9 obtained in Example 2, the antibody model was simulated by computer, and mutations were designed according to the model to obtain the variable region sequences of antibodies 13E9 H1L1, 13E9 H2L2 and 13E9 H3L2 (antibody constant region sequences are from the NCBI database, in which the heavy chain constant region is Ig gamma-1 chain C region, ACCESSION: P01857, and the light chain constant region is Ig kappa chain C region, ACCESSION: P01834).

The designed variable region sequences are as follows:
(1) heavy chain and light chain sequences of humanized monoclonal antibody 13E9 H1L1 nucleotide sequence of the heavy chain variable region: (360 bp)

(SEQ ID NO: 5)

GATGTGCAGCTGCAGGAAAGCGGACCAGGACTGGTGAAGCCTA

GCCAGACCCTGAGCCTGACTTGCACCGTGTCCAGCTACAGCTTC

ACCAGCGACTACGCTTGGTCTTGGATCAGACAGTTCCCAGGAAT

TGGCCTCGAGTGGATGGGCTACATCACCTACAGCGGCGTGACC

AGCTACAACCCCAGCCTGAAGAGCAGGATCACCATCAGCCGGG

ACACCAGCAAGAACCAGTTCTTCCTGCAGCTGAACAGCGTGAC

AGCAGCCGATACCGCAGTGTACTATTGCGCCAGGGCCGACTAC

GACAGCTACTACACCATGGACTATTGGGGCCAGGGAACCAGCG

TGACAGTGTCTAGC its encoded amino acid sequence: (120 aa)

(SEQ ID NO: 6)

DVQLQESGPGLVKPSQTLSLTCTVS<u>SYSFTSDYAWS</u>WIRQFPGIGL

EWMGY<u>ITYSGVTSYNPSLKSR</u>ITISRDTSKNQFFLQLNSVTAADTA

VYYCAR<u>ADYDSYYTMDY</u>WGQGTSVTVSS

The underlined regions are the CDR regions.

nucleotide sequence of the light chain variable region: (333 bp)

(SEQ ID NO: 7)

GATGTCGTGATGACCCAGACCCCTCTGTCTCTGCCAGTGACACT

GGGACAGCAGGCTAGCATCTCTTGCAGAAGCAGCCAGAGCCTG

GTGCACAGCAACGGCAACACCTACCTGCATTGGTACCTGCAGA

AGCCAGGCCAGTCTCCTAGACTGCTGATCTACAAGGTGTCCAA

CCGGTTCAGCGGCGTGCCAGATAGATTCAGCGGAAGCGGAAGC

GGCACCGACTTCACCCTGAAGATCAGCAGAGTGGAGGCCGAGG

ATCTGGGAGTGTACTTCTGCAGCCAGAGCACCCACTTTTGGACC

TTCGGCGGAGGCACCAAGCTGGAGATCAAG its encoded amino acid sequence: (111 aa)

(SEQ ID NO: 8)

DVVMTQTPLSLPVTLGQQASISCRSS<u>QSLVHSNGNTYLH</u>WYLQKP

GQSPRLLIY<u>KVSNRFS</u>GVPDRFSGSGSGTDFTLKISRVEAEDLGVYF

C<u>SQSTHFWT</u>FGGGTKLEIK

The underlined regions are the CDR regions.
(2) heavy chain and light chain sequences of humanized monoclonal antibody 13E9 H2L2 nucleotide sequence of the heavy chain variable region: (360 bp)

(SEQ ID NO: 9)

GATGTGCAGCTGCAGGAAAGCGGACCAGGACTGGTGAAGCCTA

GCCAGACCCTGAGCCTGACTTGCACCGTGTCCAGCTACAGCTTC

-continued

ACCAGCGACTACGCTTGGTCTTGGATCAGACAGCCACCAGGAA

AGGGACTCGAGTGGATCGGCTACATCACCTACAGCGGCGTGAC

CAGCTACAACCCCAGCCTGAAGAGCAGGATCACCATCAGCCGG

GACACCAGCAAGAACCAGTTCTTCCTGCAGCTGTCTAGCGTGA

CAGCAGCCGATACCGCAGTGTACTATTGCGCCAGGGCCGACTA

CGACAGCTACTACACCATGGACTATTGGGGCCAGGGAACCAGC

GTGACAGTGTCTAGC its encoded amino acid sequence: (120 aa)
(SEQ ID NO: 10)
DVQLQESGPGLVKPSQTLSLTCTVS<u>SYSFTSDY</u>AWSWIRQPPGKGL EWIGY<u>ITYSGVTSYNPSLKS</u>RITISRDTSKNQFFLQLSSVTAADTAV YYCAR<u>ADYDSYYTMDY</u>WGQGTSVTVSS The underlined regions are the CDR regions.

nucleotide sequence of the light chain variable
region: (333 bp)
(SEQ ID NO: 11)
GATGTCGTGATGACCCAGACCCCTCTGTCTCTGCCAGTGACACT

GGGACAGCCAGCTAGCATCTCTTGCAGAAGCAGCCAGAGCCTG

GTGCACAGCAACGGCAACACCTACCTGCATTGGTACCTGCAGA

AGCCAGGCCAGTCTCCTAGACTGCTGATCTACAAGGTGTCCAA

CCGGTTCAGCGGCGTGCCAGATAGATTCAGCGGAAGCGGAAGC

GGCACCGACTTCACCCTGAAGATCAGCAGAGTGGAGGCCGAGG

ATCTGGGAGTGTACTACTGCAGCCAGAGCACCCACTTTTGGACC

TTCGGCGGAGGCACCAAGCTGGAGATCAAG its encoded amino acid sequence: (111 aa)
(SEQ ID NO: 12)
DVVMTQTPLSLPVTLGQPASISCRSS<u>QSLVHSNGNTYLH</u>WYLQKP GQSPRLLIY<u>KVS</u>NRFSGVPDRFSGSGSGTDFTLKISRVEAEDLGVY YC<u>SQSTHFWT</u>FGGGTKLEIK The underlined regions are the CDR regions.
    (3) heavy chain and light chain sequences of humanized monoclonal antibody 13E9 H3L2 nucleotide sequence of the heavy chain variable
region: (360 bp)
(SEQ ID NO: 13)
GATGTGCAGCTGCAGGAAAGCGGACCAGGACTGGTGAAGCCTA

GCCAGACCCTGAGCCTGACTTGCACCGTGTCCAGCTACAGCTTC

ACCAGCGACTACGCTTGGTCTTGGATCAGACAGCCACCAGGAA

AGGGACTCGAGTGGATCGGCTACATCACCTACAGCGGCGTGAC

CAGCTACAACCCTAGCCTGAAGAGCCGCGTGACCATTAGCGTG

GACACCAGCAAGAACCAGTTCTCCCTGAAGCTGAGCAGCGTGA

CAGCCGCCGATACAGCAGTGTACTATTGCGCCCGGGCCGATTA

CGACAGCTACTACACCATGGACTATTGGGGCCAGGGAACCAGC

GTGACAGTGTCTAGC

Figure 3:
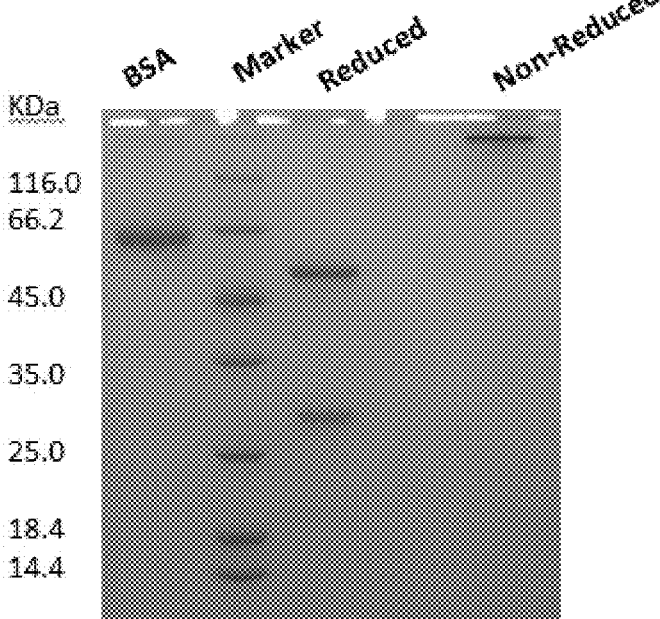
FIG. 3: SDS-PAGE detection results of monoclonal humanized antibody 13E9 H3L2. The samples of the three lanes from left to right and their respective loadings are: BSA, 1 μg; Marker, 5 μl; antibody in reducing protein electrophoresis loading buffer, 1 μg; antibody in non-reducing protein electrophoresis loading buffer, 1 μg.
Figure 4:
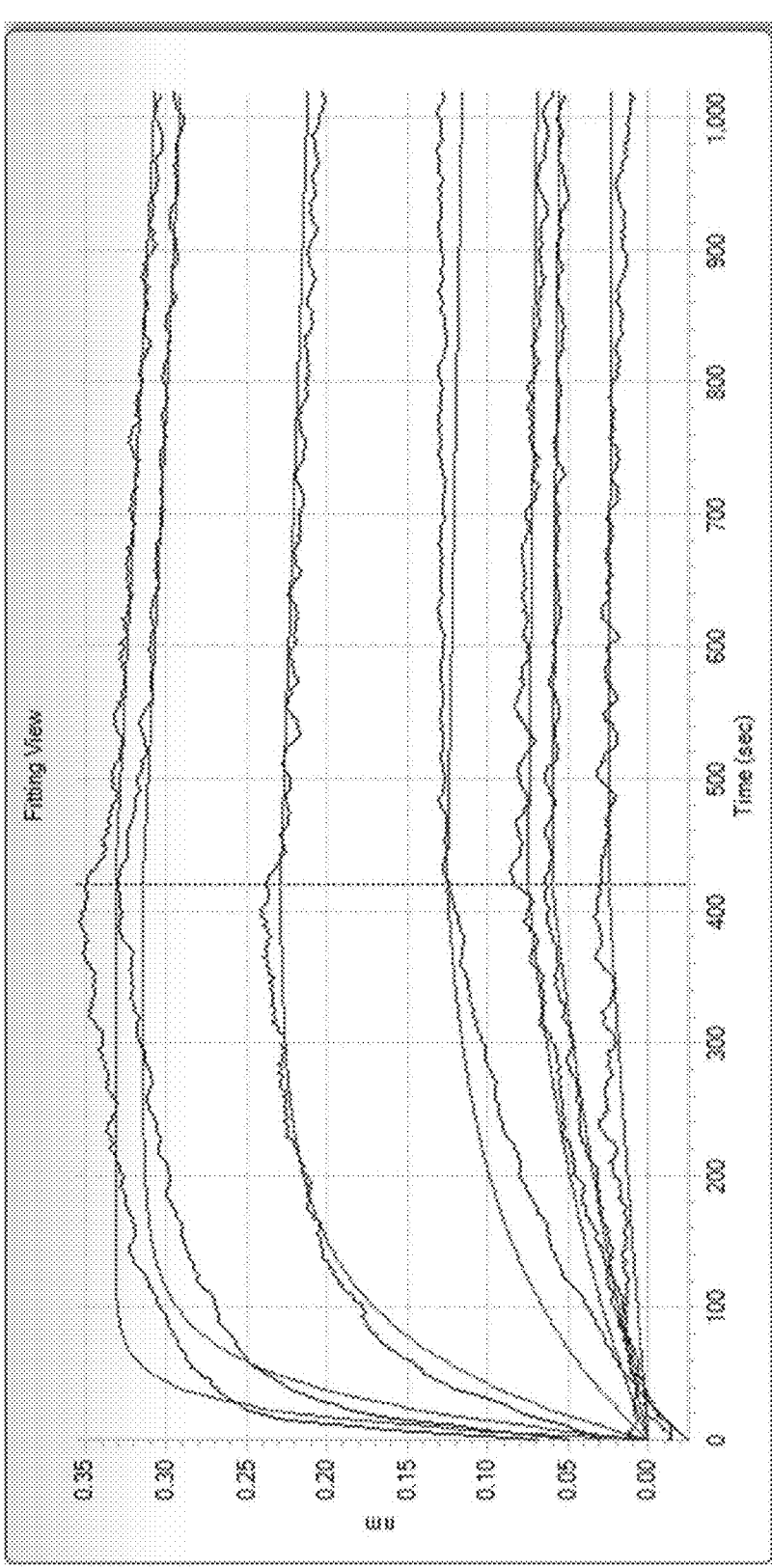
FIG. 4: detection results of the kinetic characteristic parameters of antibody 13E9 HIL1. In the figure, ordinate is signal value with nm as unit; abscissa is time with sec as unit.
Figure 5:
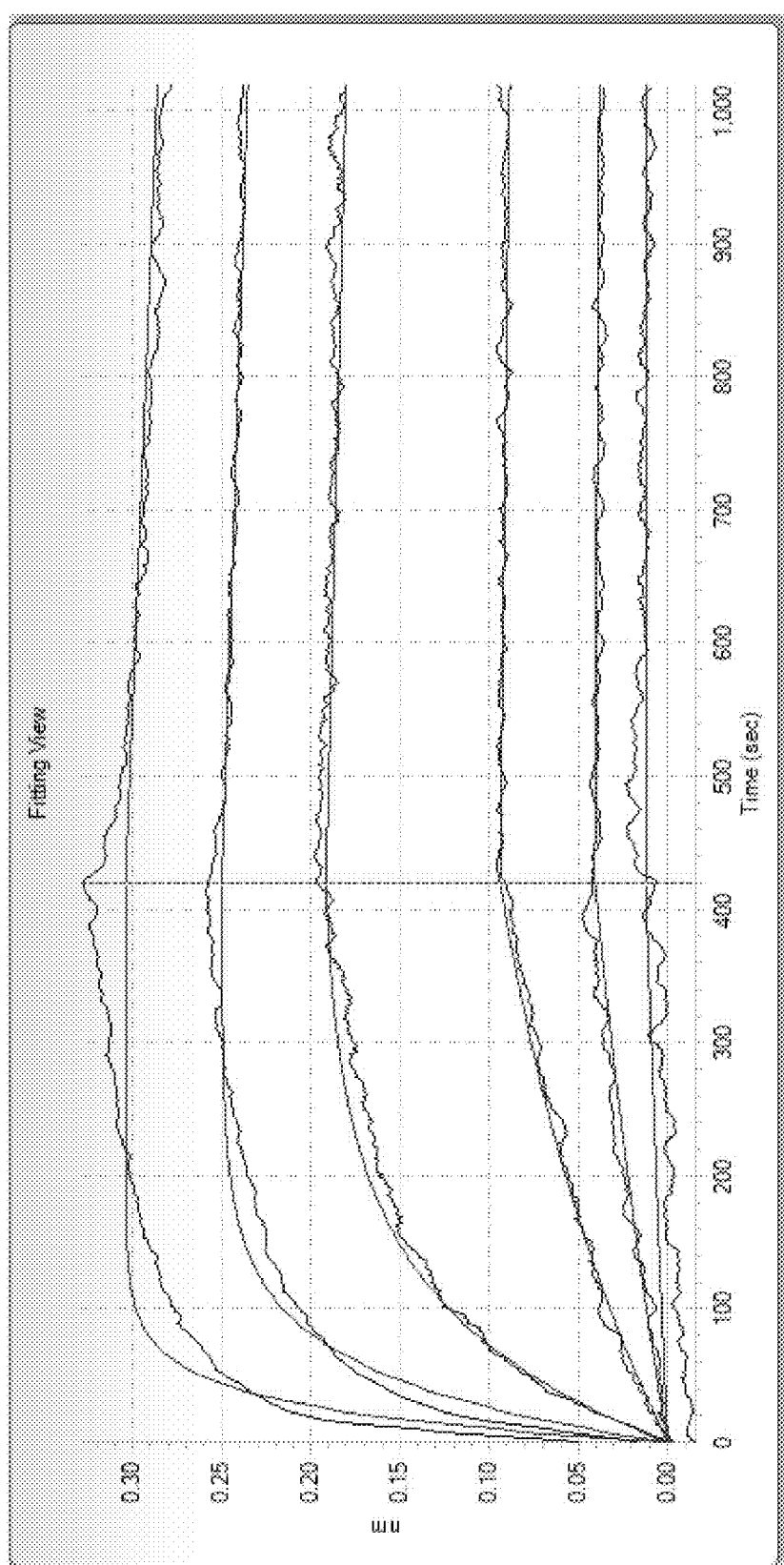
FIG. 5: detection results of the kinetic characteristic parameters of antibody 13E9 H2L2. In the figure, ordinate is signal value with nm as unit; abscissa is time with sec as unit.
Figure 6:
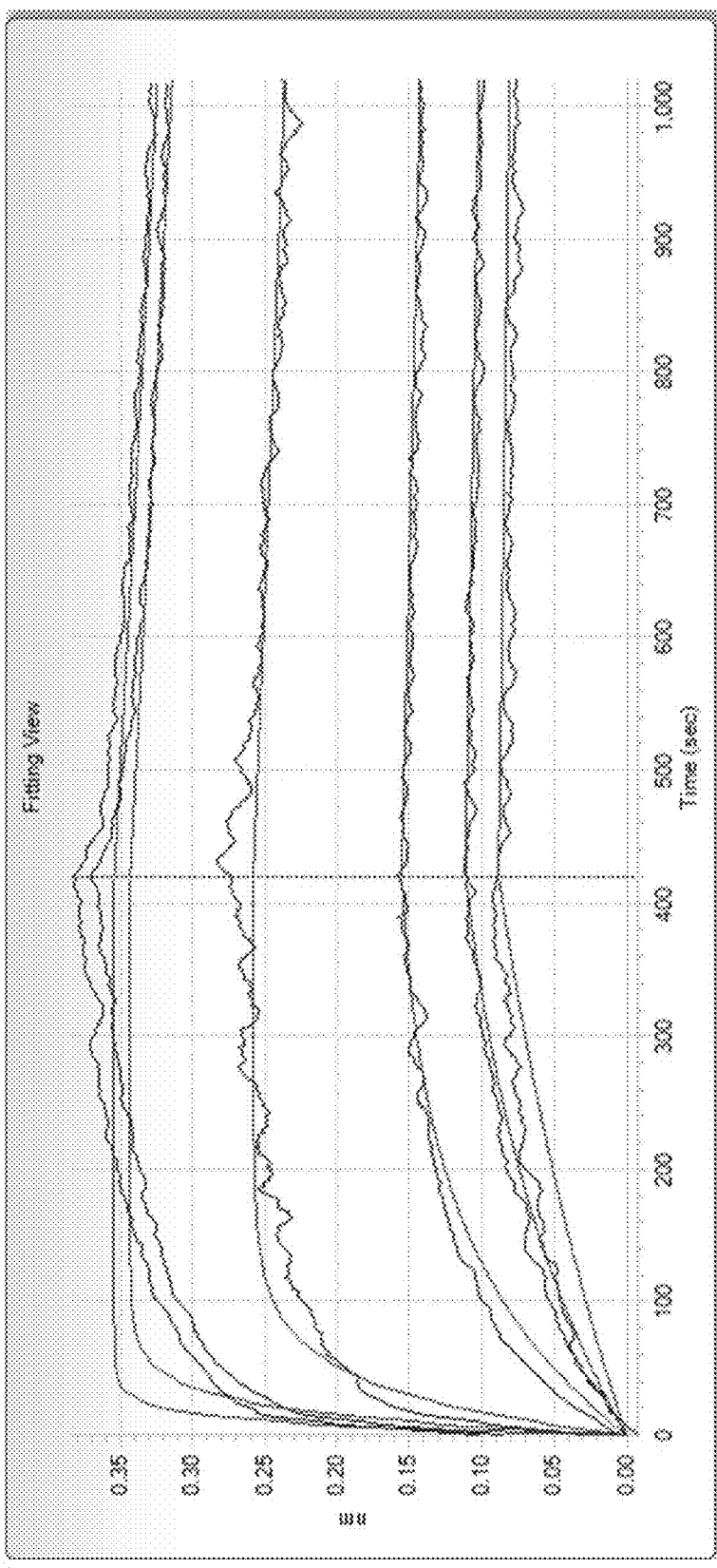
FIG. 6: detection results of the kinetic characteristic parameters of antibody 13E9 H3L2. In the figure, ordinate is signal value with nm as unit; abscissa is time with sec as unit.
Figure 7:
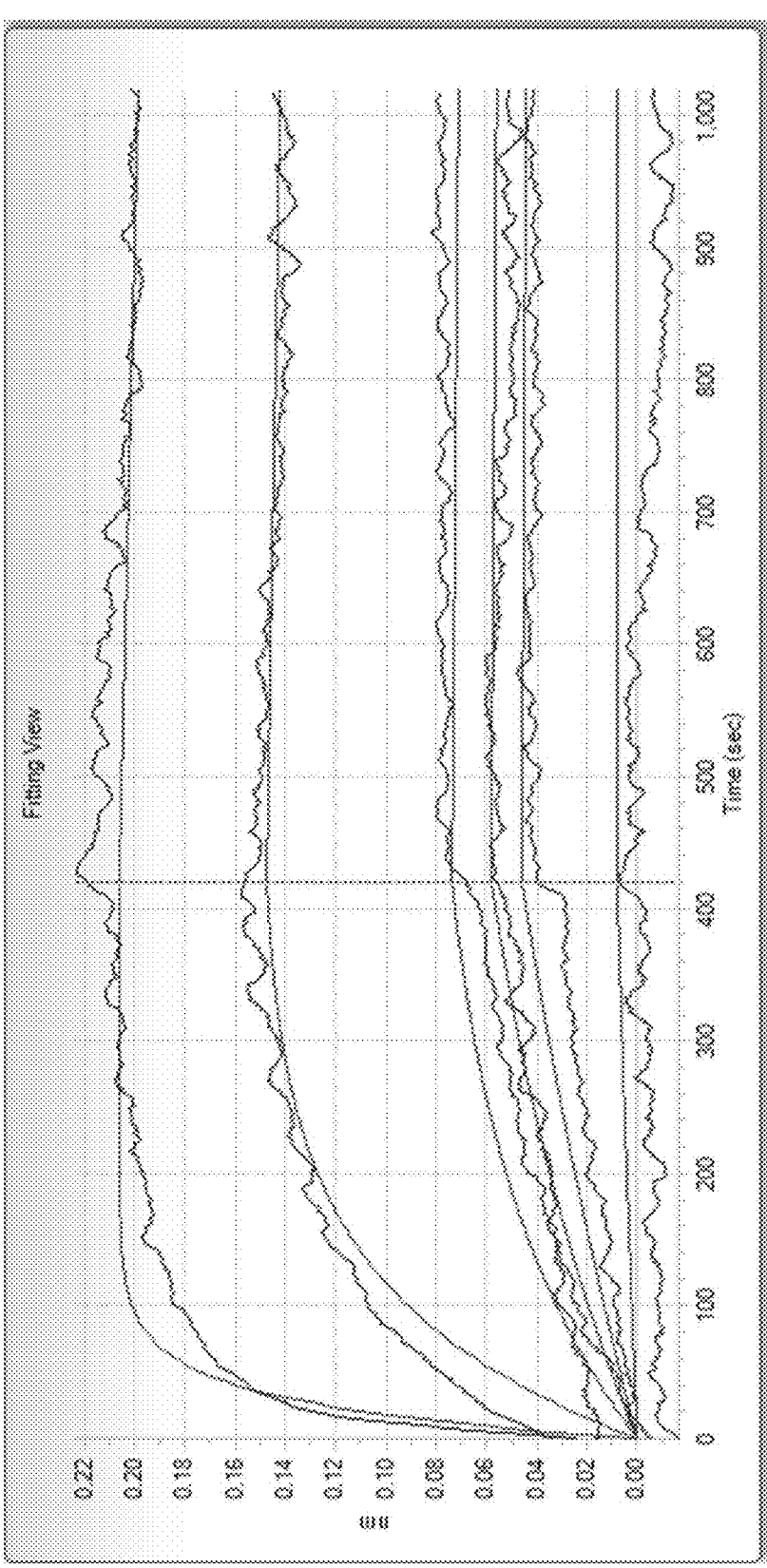
FIG. 7: detection results of the kinetic characteristic parameters of antibody Secukinumab. In the figure, ordinate is signal value with nm as unit; abscissa is time with sec as unit.
Figure 8:
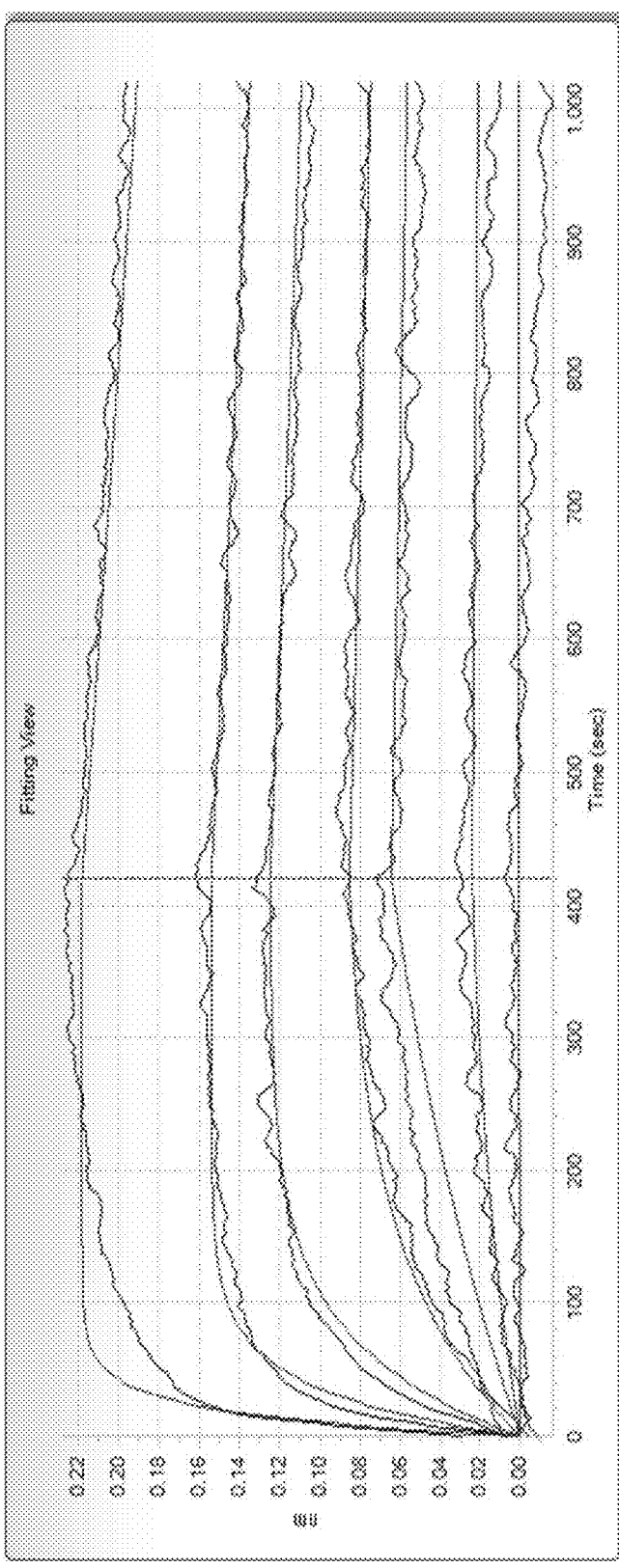
FIG. 8: detection results of the kinetic characteristic parameters of antibody 2G2 H1L1. In the figure, ordinate is signal value with nm as unit; abscissa is time with sec as unit.
Figure 9:
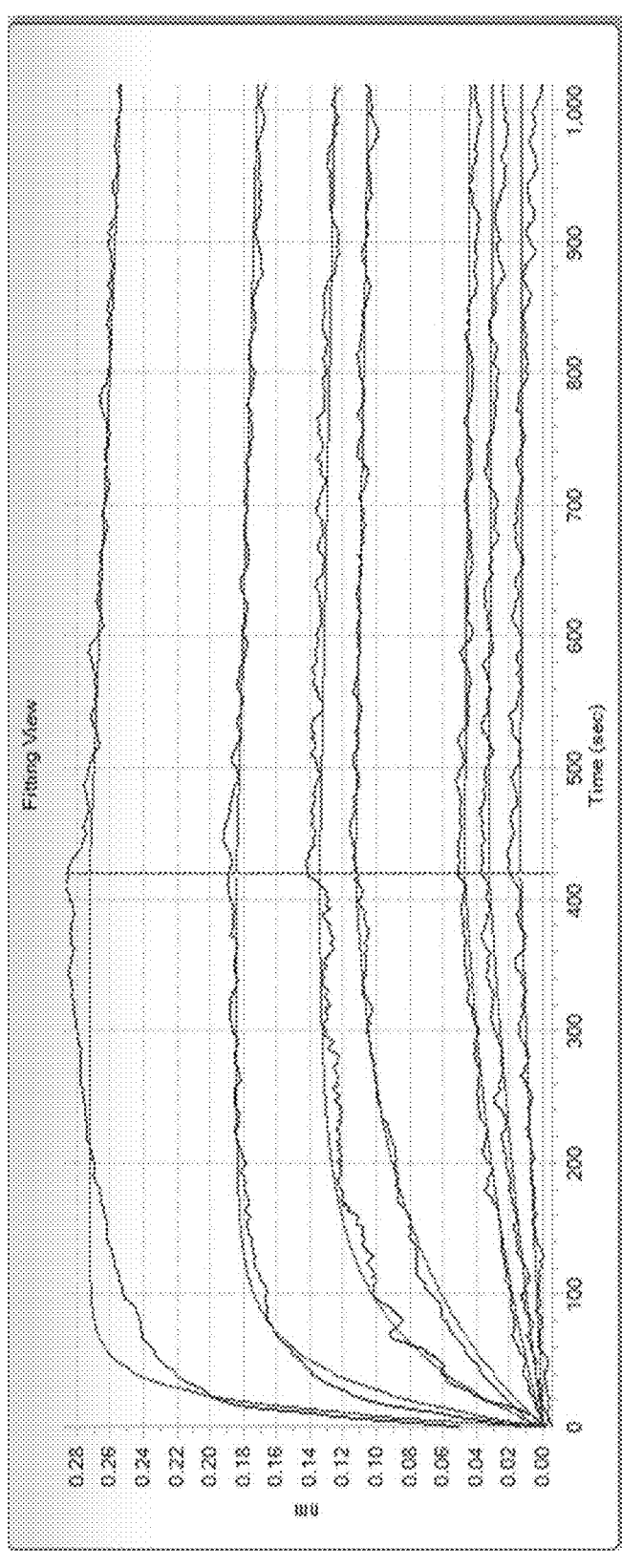
FIG. 9: detection results of the kinetic characteristic parameters of antibody 2G2 H2L2. In the figure, ordinate is signal value with nm as unit; abscissa is time with sec as unit.
Figure 10:
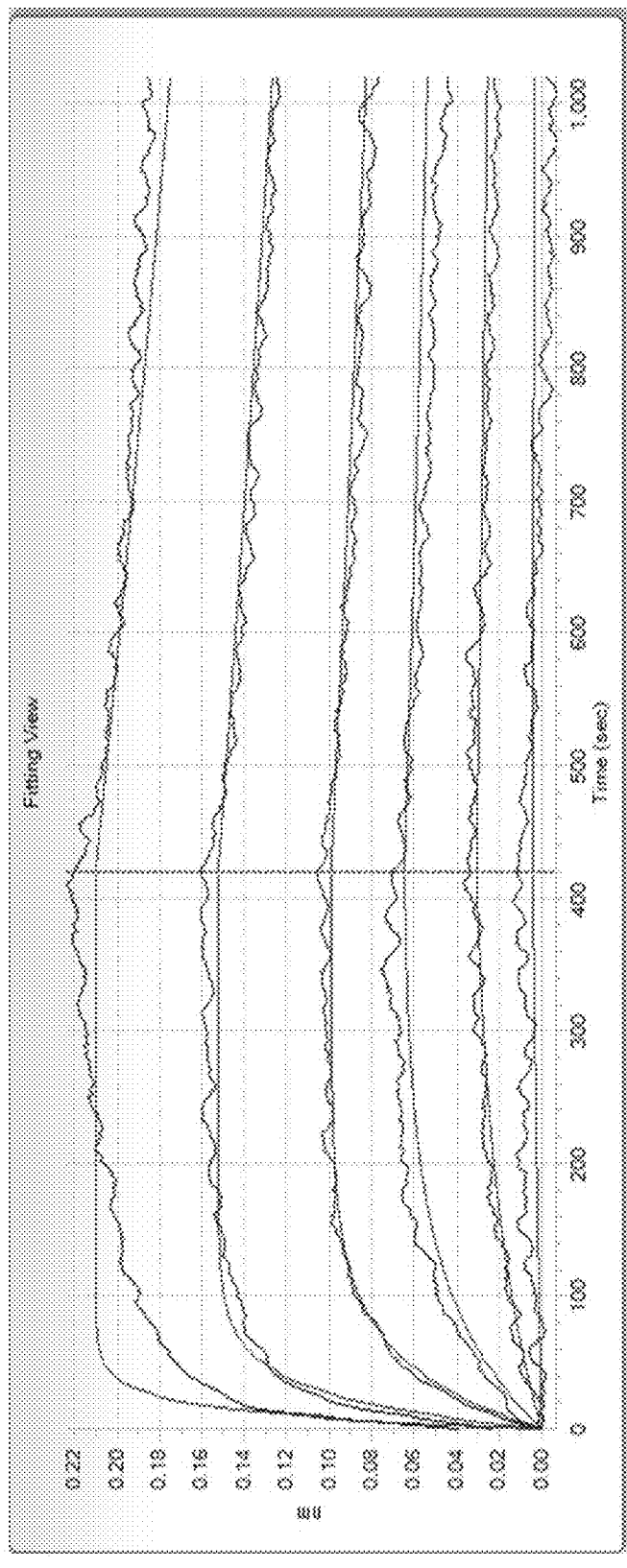
FIG. 10: detection results of the kinetic characteristic parameters of antibody 2G2 H3L3. In the figure, ordinate is signal value with nm as unit; abscissa is time with sec as unit.
Figure 11:
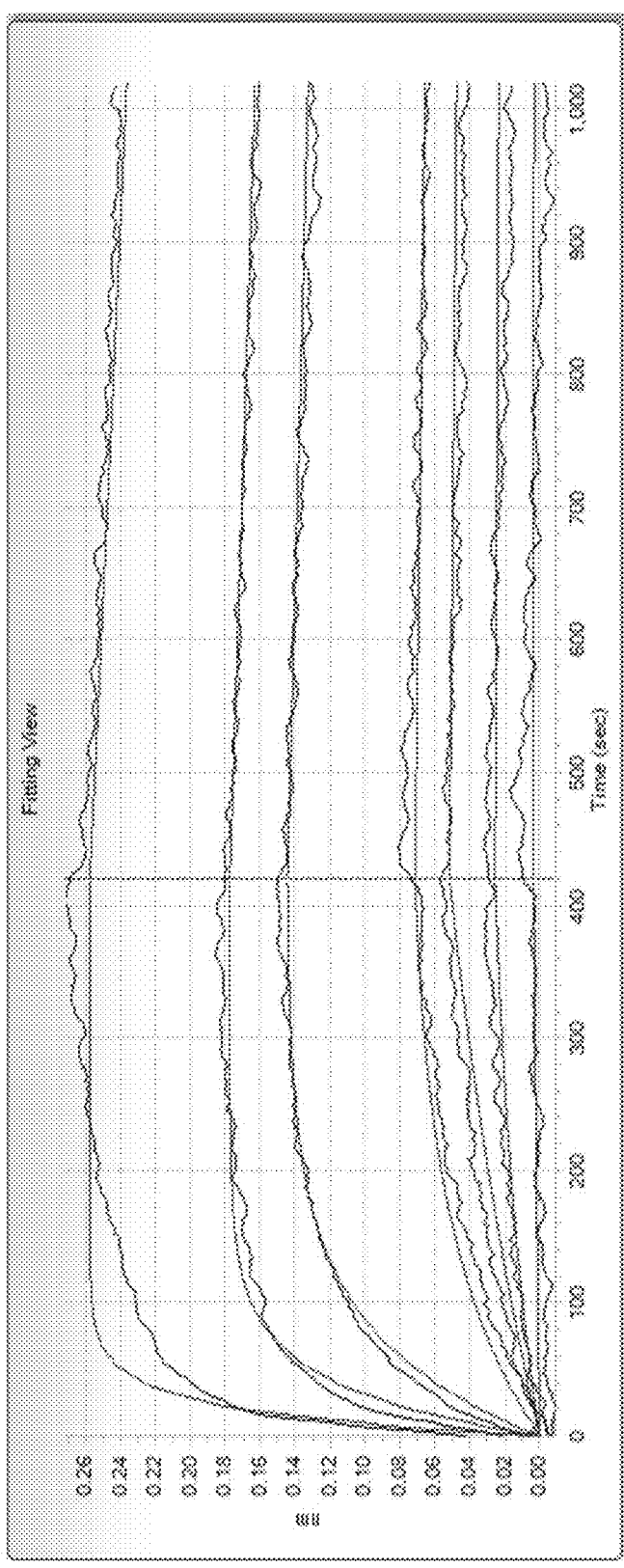
FIG. 11: detection results of the kinetic characteristic parameters of antibody Secukinumab. In the figure, ordinate is signal value with nm as unit; abscissa is time with sec as unit.

-continued
its encoded amino acid sequence: (120 aa)
(SEQ ID NO: 14)
DVQLQESGPGLVKPSQTLSLTCTVS<u>SYSFTSDY</u>AWSWIRQPPGKGL EWIGY<u>ITYSGVTSYNPSLKS</u>RVTISVDTSKNQFSLKLSSVTAADTA VYYCAR<u>ADYDSYYTMDY</u>WGQGTSVTVSS The underlined regions are the CDR regions.
    The nucleotide sequence of the light chain variable region is the same as the nucleotide sequence of the light chain variable region of 13E9 H2L2, as shown in SEQ ID NO: 11.
    Its encoded amino acid sequence is also the same as the amino acid sequence of the light chain variable region of 13E9 H2L2, as shown in SEQ ID NO: 12.
2. Preparation of Humanized Antibodies 13E9 H1L1, 13E9 H2L2 and 13E9 H3L2
    Heavy chain constant regions all use Ig gamma-1 chain C region, ACCESSION: P01857; the light chain constant regions use Ig kappa chain C region, ACCESSION: P01834.
    Heavy chain cDNA and light chain cDNA of 13E9 H1L1, heavy chain cDNA and light chain cDNA of 13E9 H2L2, and heavy chain cDNA and light chain cDNA of 13E9 H3L2 were cloned into pUC57simple (provided by Genscript) vectors, respectively, to obtain pUC57simple-13E9H1, pUC57simple-13E9L1, pUC57simple-13E9H2, pUC57simple-13E9L2 and pUC57simple-13E9H3, respectively, and fragments containing corresponding heavy chains and fragments containing corresponding light chains were subcloned into pcDNA3.1 vectors, respectively, to obtain recombinant plasmids pcDNA3.1-13E9H1, pcDNA3.1-13E9L1, pcDNA3.1-13E9H2, pcDNA3.1-13E9L2, pcDNA3.1-13E9H3 and pcDNA3.1-13E9L2. Then, the corresponding light chain recombinant plasmids and heavy chain recombinant plasmids (pcDNA3.1-13E9H1 and pcDNA3.1-13E9L1; pcDNA3.1-13E9H2 and pcDNA3.1-13E9L2; pcDNA3.1-13E9H3 and pcDNA3.1-13E9L2) were co-transfected into 293F cells, the cell culture was collected and purified to obtain humanized antibodies 13E9 H1L1, 13E9 H2L2, and 13E9 H3L2 respectively. The purified 13E9 H3L2 sample was detected by SDS-PAGE electrophoresis, and the results are shown in FIG. 3.

Example 4: Sequence Analysis of Antibody 2G2

LT007 cells were cultured according to the method in step 3 of Example 1.
    Using the cell/bacterial total RNA extraction kit (Tiangen, article number DP430), mRNA was extracted from the cultured LT007 cells according to the method in the kit manual.
    cDNA was synthesized according to the kit manual of the Invitrogen SuperScript® III First-Strand Synthesis System for RT-PCR, and amplified by PCR.
    The PCR-amplified products were directly TA cloned, and the kit manual of the pEASY-T1 Cloning Kit (Transgen CT101) was referred to for specific operations.
    The TA-cloned products were directly sequenced, and the sequencing results are as follows:

nucleotide sequence of the heavy chain variable
region: (351 bp)
(SEQ ID NO: 15)
GAGGTTCAGCTGGAGCAGTCTGGTTCTGAACTGAGGAGTCCTGGATCTTC

AGTAAAGCTTTCATGCAAGGATTTTGATTCAGAAGTCTTCCCTATTGCTGA

-continued

TATGAGTTGGGTTAGGCAGAAGCCTGGGCATGGATTTGAATGGATTGGAG

ACATACTCCCAAGTTTTGGTAGAACAATCTATGGAGAGAAGTTTGAGGAC

AAAGCCAAAGTGGATGCAGACACAGTGTCCAACACAGCCTACTTGGAAC

TCAACAGTCTGACATCTGAGGACTCTGCTATCTACTACTGTGCAAGGGGT

AACTACGGGTTTGCTTACTGGGGCCAAGGGACTCTGGTCACTGTCTCTGCA its encoded amino acid sequence: (117 aa)

(SEQ ID NO: 16)

EVQLEQSGSELRSPGSSVKLSCKDFD<u>SEVFPIADMSWVRQKPGHGFEWIG</u>

<u>DILPSFGRTI</u>YGEKFEDKAKVDADTVSNTAYLELNSLTSEDSAIYYC<u>ARG</u>

<u>NYGFAYW</u>GQGTLVTVSA

The underlined regions are the CDR regions.

nucleotide sequence of the light chain variable
region: (336 bp)

(SEQ ID NO: 17)

GATGTTTTGATGACCCAAACTCCACTCACTTTGTCGGTTATCATTGGACAA

CCAGCCTCCATCTCTTGCAAGCCAAGTCAGAGCCTCTTAAATAGTGATGG

AAAGACATATTTGAATTGGTTGTTGCAGAGGCCAGGCCAGTCTCCAAAGC

GCCTAATCTATCTGGTGTCTAAACTGGACTCTGGAGTCCCTGACAGGTTCA

CTGGCAGTGGATCAGGGACAGATTTCACACTGAAAATCAGCAGAGTGGA

GGCTGAGGATTTGGGAGTTTATTATTGCTGGCAAGGTTCACATTTTCCTCA

GACGTTCGGTGGAGGCACAAAGTTGGAAATAAAA its encoded amino acid sequence: (112 aa)

(SEQ ID NO: 18)

DVLMTQTPLTLSVIIGQPASISCKPS<u>QSLLNSDGKTYL</u>NWLLQRPGQSPKR

LIY<u>LVS</u>KLDSGVPDRFTGSGSGTDFTLKISRVEAEDLGVYYC<u>WQGSHFPQT</u>

<u>F</u>GGGTKLEIK

The underlined regions are the CDR regions.

Example 5: Design, Preparation and Detection of
Anti-IL-17A Humanized Antibodies 2G2 H1L1,
2G2 H2L2 and 2G2 H3L3

(1) heavy chain and light chain sequences of humanized
monoclonal antibody 2G2 H1L1 nucleotide sequence of the heavy chain variable
region: (348 bp)

(SEQ ID NO: 19)

GTGCAGCTGGTGCAGAGCGGAAGCGAACTGAGAAAGCCAGGCTCCAG

CGTGAAGCTGTCTTGCAAGGACTTCGACAGCGAGGTGTTCCCCATCGC

CGATATGTCTTGGGTCCGACAGGCTCCAGGCCAGGGATTCGAGTGGAT

CGGTGACATTCTGCCCAGCTTCGGAAGAACCAACTACGCCCAGAAGTT

CGAGGGCAAGGCCAAGGTGGACGCAGACAAGAGCACCAACACCGCCT

ACCTGGAGCTGAACAGCCTGAGAAGCGAGGACACCGCCATCTACTAT

TGCGCCAGGGGCAACTACGGATTCGCCTATTGGGGCCAGGGAACACT

GGTGACAGTGTCCGCC

-continued its encoded amino add sequence: (116 aa)

(SEQ ID NO: 20)

VQLVQSGSELRKPGSSVKLSCKDFD<u>SEVFPIADMSWVRQAPGQGFEWIGD</u>

<u>ILPSFGRT</u>NYAQKFEGKAKVDADKSTNTAYLELNSLRSEDTAIYYC<u>ARGN</u>

<u>YGFAY</u>WGQGTLVTVSA

The underlined regions are the CDR regions.

nucleotide sequence of the light chain variable
region: (336 bp)

(SEQ ID NO: 21)

GATGTCGTGATGACCCAGACCCCTCTGTCTCTGAGCGTGACACTGGGA

CAGCCAGCTAGCATCAGCTGCAGAAGCAGCCAGAGCCTGCTGAACAG

CGACGGCAAGACCTACCTGAATTGGCTGCTGCAGAGACCAGGCCAGT

CTCCTAGAAGGCTGATCTACCTGGTGTCCAAGCTGGACAGCGGCGTGC

CAGATAGATTCAGCGGAAGCGGAAGCGGCACCGACTTCACCCTGAAG

ATCAGCAGAGTGGAGGCCGAGGATCTGGGAGTGTACTACTGTTGGCA

GGGCAGCCACTTCCCTCAGACATTCGGCGGCGGCACAAAGCTGGAGA

TCAAG its encoded amino acid sequence: (112 aa)

(SEQ ID NO: 22)

DVVMTQTPLSLSVTLGQPASISCRSS<u>QSLLNSDGKTYL</u>NWLLQRPGQSPR

RLIY<u>LVS</u>KLDSGVPDRFSGSGSGTDFTLKISRVEAEDLGVYYC<u>WQGSHFP</u>

<u>QT</u>FGGGTKLEIK

The underlined regions are the CDR regions.

(2) heavy chain and light chain sequences of humanized
monoclonal antibody 2G2 H2L2 nucleotide sequence of the heavy chain variable
region: (348 bp)

(SEQ ID NO: 23)

GTGCAGCTGGTGCAGAGCGGAGCAGAAGTGAAGAAGCCAGGCTCCAG

CGTGAAGCTGTCTTGCAAGGACTTCGACAGCGAGGTGTTCCCCATCGC

CGATATGTCTTGGGTCCGACAGGCTCCAGGCCAGGGATTCGAGTGGAT

CGGTGACATTCTGCCCAGCTTCGGGAGAACCAATTACGCCCAGAAGTT

CCAGGGCAGAGTGACCGTGACCGCAGACAAGAGCACCAACACCGCCT

ACCTGGAGCTGAACAGCCTGAGGAGCGAGGATACCGCCGTGTACTATT

GCGCCAGGGGCAACTACGGCTTCGCCTATTGGGGACAGGGAACACTG

GTGACAGTGTCCGCC its encoded amino acid sequence: (116 aa)

(SEQ ID NO: 24)

VQLVQSGAEVKKPGSSVKLSCKDFD<u>SEVFPIADMSWVRQAPGQGFEWIG</u>

<u>DILPSFGRT</u>NYAQKTQGRVTVTADKSTNTAYLELNSLRSEDTAVYYC<u>ARG</u>

<u>NYGFAYW</u>GQGTLVTVSA

The underlined regions are the CDR regions.

nucleotide sequence of the light chain variable
region: (336 bp)

```
                                (SEQ ID NO: 25)
GATGTCGTGATGACCCAGACCCCTCTGTCTCTGAGCGTGACACTGGGA

CAGCCAGCTAGCATCAGCTGCAGAAGCAGCCAGAGCCTGCTGAACAG

CGACGGCAAGACCTACCTGAATTGGCTGCTGCAGAGACCAGGCCAGT

CTCCTAGAAGGCTGATCTACCTGGTGTCCAACCTGGACAGCGGCGTGC

CAGATAGATTCAGCGGAAGCGGAAGCGGCACCGACTTCACCCTGAAG

ATCAGCAGAGTGGAAGCCGAGGACGTGGGAGTGTACTACTGTTGGCA

GGGCAGCCACTTCCCTCAGACATTCGGCGGCGGCACAAAGCTGGAGA

TCAAG
``` its encoded amino acid sequence: (112 aa)

```
                                (SEQ ID NO: 26)
DVVMTQTPLSLSVTLGQPASISCRSSQSLLNSDGKTYLNWLLQRPGQSPR

RLIYLVSNLDSGVPDRFSGSGSGTDFTLKISRVEAEDVGVYYCWQGSHFP

QTFGGGTKLEIK
```

The underlined regions are the CDR regions.

(3) heavy chain and light chain sequences of humanized monoclonal antibody 2G2 H3L3 nucleotide sequence of the heavy chain variable
region: (348 bp)

```
                                (SEQ ID NO: 27)
GTGCAGCTGGTGCAGAGCGGAGCAGAAGTGAAGAAGCCAGGCAGCAG

CGTGAAGGTGTCTTGCAAGGACTTCAGCAGCGAGGTGTTCCCCATCGC

CGATATGTCTTGGGTCCGACAGGCTCCAGGCCAGGGACTGGAGTGGAT

CGGTGACATTCTGCCCAGCTTCGGGAGAACCAATTACGCCCAGAAGTT

CCAGGGCAGAGTGACCGTGACCGCAGACAAGAGCACCAACACCGCCT

ACCTGGAGCTGTCTAGCCTGAGAAGCGAGGACACCGCCGTGTACTATT

GCGCCAGGGGCAACTACGGCTTCGCCTATTGGGGACAGGGAACACTG

GTGACAGTGTCCGCC
``` its encoded amino acid sequence: (116 aa)

```
                                (SEQ ID NO: 28)
VQLVQSGAEVKKPGSSVKVSCKDFSSEVFPIADMSWVRQAPGQGLEWIG

DILPSFGRTNYAQKFQGRVTVTADKSTNTAYLELSSLRSEDTAVYYCARG

NYGFAYWGQGTLVTVSA
```

The underlined regions are the CDR regions.

nucleotide sequence of the light chain variable
region: (336 bp)

```
                                (SEQ ID NO: 29)
GATGTCGTGATGACCCAGACCCCTCTGTCTCTGAGCGTGACACTGGGA

CAGCCAGCTAGCATCAGCTGCAGAAGCAGCCAGAGCCTGCTGAACAG

CGACGGCAAGACCTACCTGAATTGGTTCCTGCAGAGACCAGGCCAGTC

TCCTAGAAGGCTGATCTACCTGGTGTCCAACCTGGACAGCGGCGTGCC

AGATAGATTCAGCGGAAGCGGAAGCGGCACCGACTTCACCCTGAAGA

TCAGCAGAGTGGAAGCCGAGGACGTGGGAGTGTACTACTGTTGGCAG
```

-continued

```
GGCAGCCACTTCCCTCAGACATTCGGCGGCGGCACAAAGCTGGAGAT

CAAG
``` its encoded amino acid sequence: (112 aa)

```
                                (SEQ ID NO: 30)
DVVMTQTPLSLSVTLGQPASISCRSSQSLLNSDGKTYLNWFLQRPGQSPR

RLIYLVSNLDSGVPDRFSGSGSGTDFTLKISRVEAEDVGVYYCWQGSHFP

QTFGGGTKLEIK
```

The underlined regions are the CDR regions.

2. Preparation and SDS-PAGE Electrophoresis Detection of Humanized Antibodies 2G2 H1L1, 2G2 H2L2 and 2G2 H3L3

Heavy chain constant regions used Ig gamma-1 chain C region, ACCESSION: P01857; the light chain constant regions used Ig kappa chain C region, ACCESSION: P01834.

Heavy chain cDNA and light chain cDNA of 2G2 H1L1, heavy chain cDNA and light chain cDNA of 2G2 H2L2, and heavy chain cDNA and light chain cDNA of 2G2 H3L3 were cloned into pUC57simple (provided by Genscript) vectors, respectively, to obtain pUC57simple-2G2H1, pUC57simple-2G2L1; pUC57simple-2G2H2, pUC57simple-2G2L2; and pUC57simple-2G2H3, pUC57simple-2G2L3, respectively. Nucleotide fragments containing corresponding heavy chains and nucleotide fragments containing corresponding light chains were then subcloned into pcDNA3.1 vectors, respectively, to obtain recombinant plasmids pcDNA3.1-2G2H1, pcDNA3.1-2G2L1, pcDNA3.1-2G2H2, pcDNA3.1-2G2L2, pcDNA3.1-2G2H3 and pcDNA3.1-2G2L3. Then, the corresponding light chain recombinant plasmids and heavy chain recombinant plasmids (pcDNA3.1-2G2H1 and pcDNA3.1-2G2L1; pcDNA3.1-2G2H2 and pcDNA3.1-2G2L2; pcDNA3.1-2G2H3 and pcDNA3.1-2G2L3) were co-transfected into 293F cells, the cell culture was collected and purified to obtain humanized antibodies 2G2 H1L1, 2G2 H2L2 and 2G2 H3L3 respectively. The purified samples were detected by SDS-PAGE electrophoresis.

Example 6: Measurement of Kinetic Parameters for the Binding of 13E9 H1L1, 13E9 H2L2 and 13E9 H3L2 to the Antigen IL-17A (24-155) Protein The kinetic parameters for the binding of humanized antibodies 13E9 H1L1, 13E9 H2L2 and 13E9 H3L2 to the antigen IL-17A (24-155) were measured using a Fortebio molecular interaction instrument.

The AR2G sensor was activated by EDC/NHS, and the antibody was fixed to the activated AR2G sensor by amine coupling, and the sensor was blocked with 1 M ethanolamine (pH 8.5). After the sensor was equilibrated in PBST for 300 s, the antibody fixed on the sensor binded to the antigen IL-17A (24-155) protein (same as the antigen used in Example 1), in which the antigen concentration was 6.25-400 nM (double gradient dilution) and the binding time was 420 s, and the antigen and the antibody were dissociated in PBST for 600 s.

The kinetic parameters of antibodies 13E9 H1L1, 13E9 H2L2, 13E9 H3L2 and Secukinumab are shown in Table 1, and detection results of the kinetic characteristic parameters are shown in FIG. 4, FIG. 5, FIG. 6 and FIG. 7, respectively.

TABLE 1

| the kinetic parameters of 13E9 humanized antibody | | | | | |
|---|---|---|---|---|---|
| Antibody | $K_D$ (M) | Kon (1/Ms) | Kon error | Kdis (1/s) | Kdis error | $R_{max}$ (nm) |
| 13E9 H1L1 | 9.72E−10 | 1.34E+05 | 2.60E+03 | 1.31E−04 | 9.06E−06 | 0.0858 − 0.3326 |
| 13E9 H2L2 | 1.03E−09 | 9.86E+04 | 1.51E+03 | 1.01E−04 | 7.57E−06 | 0.0546 − 0.3049 |
| 13E9 H3L2 | 5.08E−10 | 2.90E+05 | 8.22E+03 | 1.47E−04 | 1.02E−05 | 0.1457 − 0.3546 |
| Secukinumab | 6.74E−10 | 9.28E+04 | 3.03E+03 | 6.26E−05 | 1.57E−05 | 0.0379 − 0.2064 |

KD is affinity constant; Kon is binding rate of antigen and antibody; Kdis is dissociation rate of antigen and antibody; KD=Kdis/Kon.

The results show that 13E9 H1L1, 13E9 H2L2, and 13E9 H3L2 all have good affinity to the antigen IL-17A (24-155), and the affinity is equivalent to that of the control antibody Secukinumab.

Example 7: Measurement of Kinetic Parameters for the Binding of 2G2 H1L1, 2G2 H2L2, and 2G2 H3L3 to the Antigen IL-17A (24-155)

The kinetic parameters for the binding of humanized antibodies 2G2 H1L1, 2G2 H2L2 and 2G2 H3L3 to the antigen IL-17A (24-155) were measured using a Fortebio molecular interaction instrument.

The AR2G sensor was activated by EDC/NHS, and the antibody was fixed to the activated AR2G sensor by amine coupling, and the sensor was blocked with 1 M ethanolamine (pH 8.5). After the sensor is equilibrated in PBST for 300 s, the antibody fixed on the sensor bound to the antigen IL-17A (24-155), in which the antigen concentration was 6.25-400 nM (double gradient dilution) and the binding time was 420 s, and the antigen and the antibody were dissociated in PBST for 600 s.

The kinetic parameters of antibodies 2G2 H1L1, 2G2 H2L2, 2G2 H3L3, and Secukinumab are shown in Table 2, and detection results of the kinetic characteristic parameters are shown in FIG. 8, FIG. 9, FIG. 10, and FIG. 11, respectively.

IL17A-His can be prepared by referring to the published sequences and conventional technical means in the art, or referring to the following steps:

Preparation of IL17A-His: the full-length protein sequence of human IL-17A was found in the NCBI protein database, and fused with His*6 purification tag. Genscript in Nanjing was entrusted to synthesize the nucleic acid encoding the fusion protein, and by referring to the standard technologies introduced in the *Guide to Molecular Cloning Experiments* (*Second Edition*) and using standard molecular cloning technologies such as PCR, enzyme digestion, gel recovery, ligation transformation, colony PCR or enzyme digestion identification, the target gene was subcloned into mammalian cell expression vectors, and the target gene with the recombinant expression vectors was further sequenced and analyzed. After the sequence was verified to be correct, a medium and large amount of endotoxin-free expression plasmids were prepared, and transiently transfected HEK293 cells for protein expression. After 7 days of culture, the cell culture fluid was collected and affinity purified using a Ni SEPHAROSE™ column (GE), and the quality of the resulting protein samples was determined using SDS-PAGE and SEC-HPLC standard analysis techniques to be up to standard.

TABLE 2

| the kinetic parameters of 2G2 H1L1, 2G2 H2L2, 2G2 H3L3 and Secukinumab | | | | | |
|---|---|---|---|---|---|
| Antibody | $K_D$ (M) | Kon(1/Ms) | Kon error | Kdis (1/s) | Kdis error | Rmax(nm) |
| 2G2 H1L1 | 1.53E−09 | 1.46E+05 | 3.15E+03 | 2.24E−04 | 9.67E−06 | 0.0035 − 0.2192 |
| 2G2 H2L2 | 8.43E−10 | 1.42E+05 | 2.18E+03 | 1.20E−04 | 6.73E−06 | 0.0444 − 0.2732 |
| 2G2 H3L3 | 1.54E−09 | 1.98E+05 | 5.30E+03 | 3.06E−04 | 1.08E−05 | 0.011 − 0.2109 |
| Secukinumab | 1.08E−09 | 1.33E+05 | 2.38E+03 | 1.43E−04 | 8.09E−06 | 0.0118 − 0.2584 |

KD is affinity constant; Kon is binding rate of antigen and antibody; Kdis is dissociation rate of antigen and antibody; KD=Kdis/Kon.

The results show that compared with the control antibody Secukinumab, 2G2 H2L2 has a higher affinity to the antigen IL-17A (24-155); the affinity of 2G2 H1L1 and 2G2 H3L3 is equivalent to that of the control antibody Secukinumab.

Example 8: Detection of the Binding Activity of the Antibodies 13E9 H1L1, 13E9 H2L2 and 13E9 H3L2 to the Antigen with an ELISA Method 1. The binding activity of the antibodies 13E9 H1L1, 13E9 H2L2 and 13E9 H3L2 to the antigen IL17A-His was detected with an indirect ELISA and compared with the marketed drug Secukinumab for the same target.

ELISA: IL17A-His was added to the microplate and incubated at 4° C. overnight; after blocking with 1% BSA in PBS at 37° C. for 2 h, antibodies were added respectively, and incubated at 37° C. for 30 min; and Goat Anti Human IgG (H+L)-HRP (Jackson, 109-035-088) was added and incubated at 37° C. for 30 min; and then the color reaction was performed with TMB (Neogen, 308177) for 5 min, and the absorbance at 450 nm was detected in a microplate reader. The obtained experimental data were analyzed and processed with SoftMax Pro 6.2.1 software, and the 4-parameter fitted curve was plotted for analysis with the antibody concentration as the abscissa and the absorbance value as the ordinate.

Figure 12:
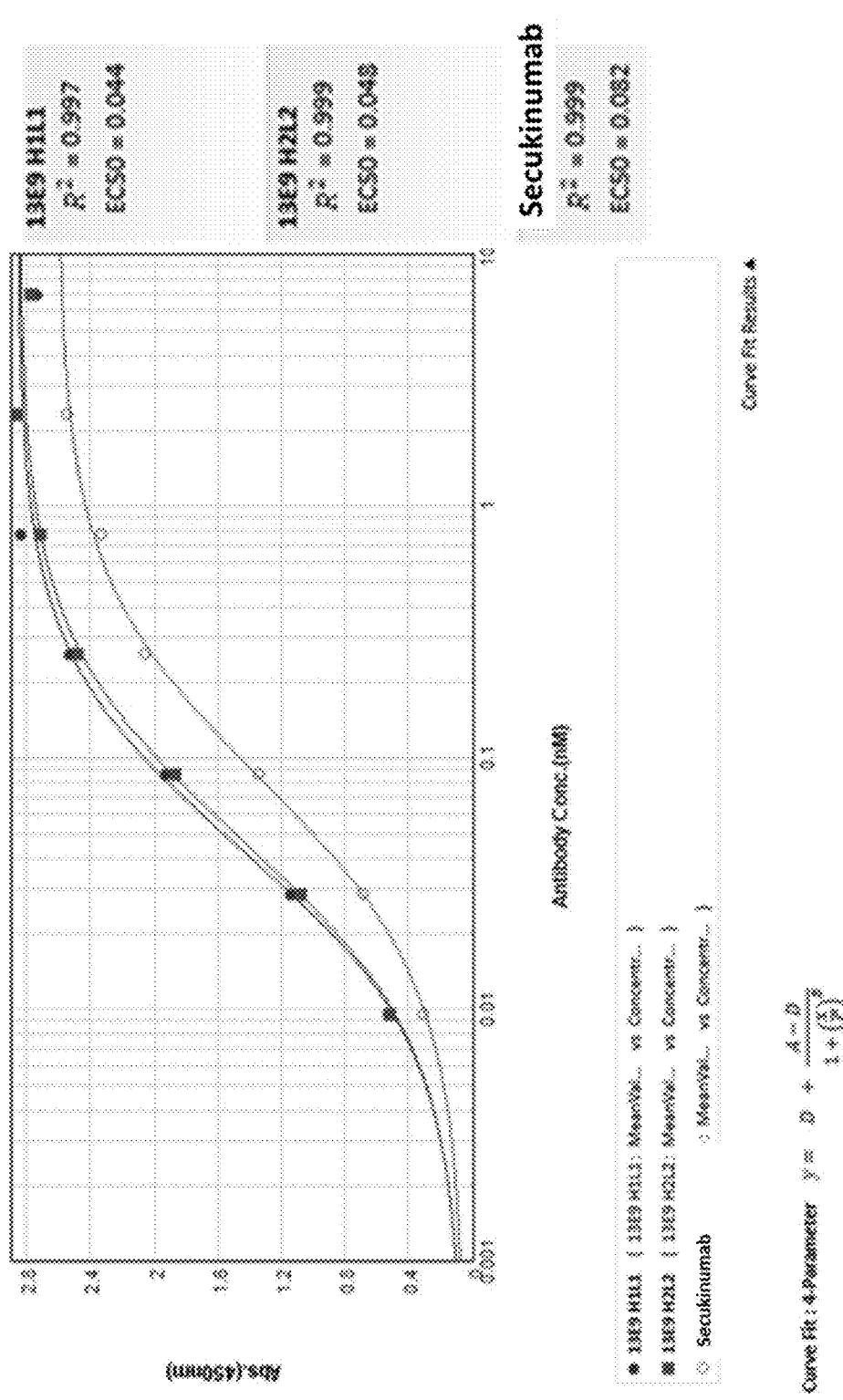
FIG. 12: detection of the binding activity of antibodies 13E9 H1L1 and 13E9 H2L2 to antigen IL17A-His with an indirect ELISA method. The marketed drug Secukinumab is used as a positive control.
Figure 13:
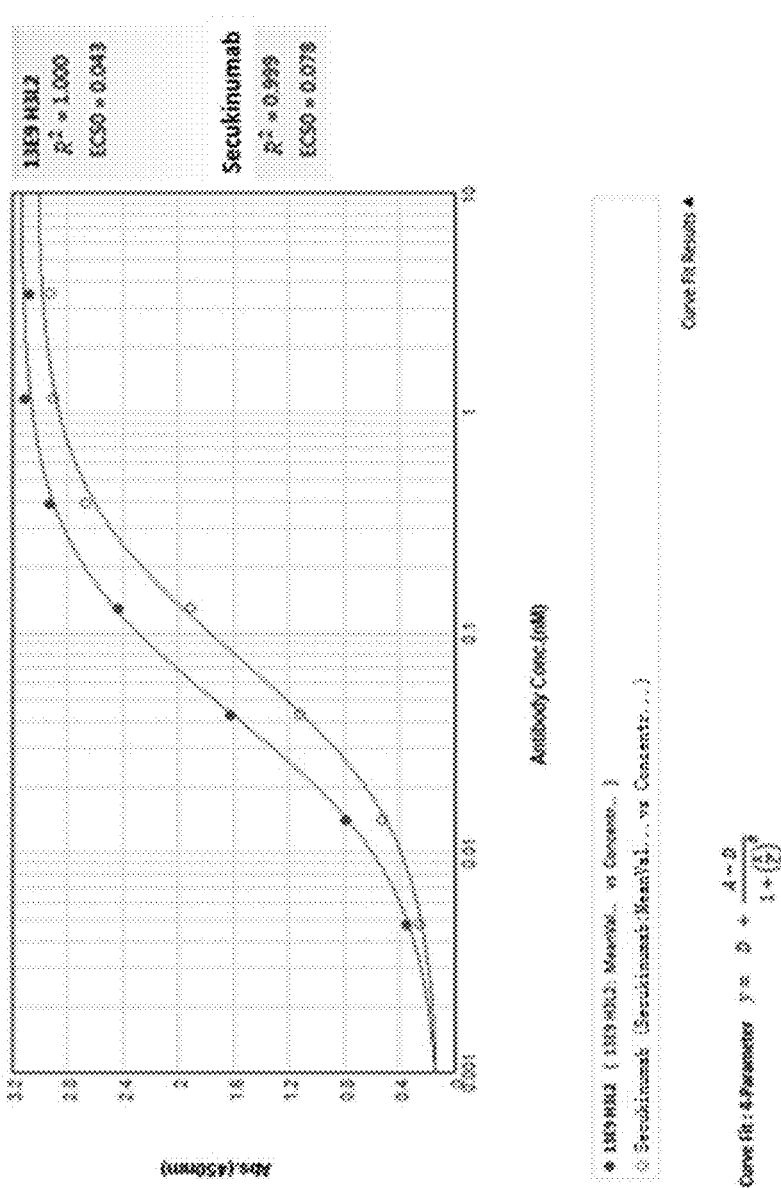
FIG. 13: detection of the binding activity of antibody 13E9 H3L2 to antigen IL17A-His by indirect ELISA method. The marketed drug Secukinumab is used as a positive control.

The experimental results are shown in FIG. 12, FIG. 13, and Table 3 and Table 4 below.

TABLE 3 detection results of the binding activity of 13E9
H1L1 and 13E9 H2L2 to the antigen IL17A-His

| Antibody concentration/ gradient | Coating antigen: IL17A-His, 1 µg/mL | | | | | |
|---|---|---|---|---|---|---|
| | 13E9 H1L1 | | 13E9 H2L2 | | Secukinumab | |
| 1 µg/mL | 2.726 | 2.731 | 2.804 | 2.737 | 2.184 | 2.227 |
| 1:3 | 2.875 | 2.852 | 2.832 | 2.873 | 2.595 | 2.505 |
| 1:9 | 2.858 | 2.815 | 2.717 | 2.712 | 2.297 | 2.364 |
| 1:27 | 2.564 | 2.494 | 2.479 | 2.481 | 2.049 | 2.064 |
| 1:81 | 1.934 | 1.925 | 1.891 | 1.834 | 1.372 | 1.314 |
| 1:243 | 1.159 | 1.116 | 1.097 | 1.062 | 0.672 | 0.697 |
| 1:729 | 0.522 | 0.537 | 0.514 | 0.511 | 0.313 | 0.309 |
| 0 | 0.047 | 0.048 | 0.048 | 0.048 | 0.046 | 0.046 |
| $EC_{50}$ (nM) | 0.044 | | 0.048 | | 0.082 | |

TABLE 4 detection results of the binding activity
of 13E9 H3L2 to the antigen IL17A-His

| Antibody concentration/ gradient | Coating antigen: IL17A-His: 1 µg/mL | | | |
|---|---|---|---|---|
| | 13E9 H3L2 | | Secukinumab | |
| 0.5 µg/mL | 3.074 | 3.068 | 2.929 | 2.929 |
| 1:3 | 3.175 | 3.026 | 2.924 | 2.885 |
| 1:9 | 2.944 | 2.895 | 2.660 | 2.666 |
| 1:27 | 2.472 | 2.393 | 1.947 | 1.862 |
| 1:81 | 1.610 | 1.617 | 1.140 | 1.092 |
| 1:243 | 0.786 | 0.783 | 0.521 | 0.522 |
| 1:729 | 0.343 | 0.348 | 0.252 | 0.253 |
| 0 | 0.091 | 0.084 | 0.087 | 0.087 |
| $EC_{50}$ (nM) | 0.043 | | 0.078 | |

The experimental results show that the antibodies 13E9 H1L1, 13E9 H2L2 and 13E9 H3L2 all can effectively bind to the antigen IL17A-His, and their binding efficiency is dose-dependent. Under the same experimental conditions, the binding EC50 of 13E9 H1L1 is 0.044 nM, the binding EC50 of 13E9 H2L2 is 0.048 nM, and the EC50 of the marketed drug Secukinumab for the same target is 0.082 nM (FIG. 12, Table 3); under the same experimental conditions, the binding EC50 of 13E9 H3L2 is 0.043 nM, and the EC50 of the marketed drug Secukinumab for the same target is 0.078 nM (FIG. 13, Table 4).

The above experimental results show that under the same experimental conditions, the $EC_{50}$ values of 13E9 H1L1, 13E9 H2L2 and 13E9 H3L2 are all smaller than those of the positive control drug Secukinumab for the same target, indicating that the binding activity of 13E9 H1L1, 13E9 H2L2 and 13E9 H3L2 to IL17A-His is better than that of the marketed control drug Secukinumab for the same target.

2. The activity of antibodies 13E9 H1L1, 13E9 H2L2 and 13E9 H3L2 blocking the binding of IL17RA-His (biotin) to the antigen IL17A-His is detected with a competitive ELISA.

IL17RA-His (biotin) can be prepared by referring to the published sequences and conventional technical means in the art, or referring to the following steps:

Preparation of IL17RA-His (biotin): the extracellular domain sequence of human IL-17RA was found in the NCBI protein database, and fused with His*6 purification tag. Genscript in Nanjing was entrusted to synthesize the nucleic acid encoding the fusion protein, and by referring to the standard technologies introduced in the *Guide to Molecular*

*Cloning Experiments* (*Second Edition*) and using standard molecular cloning technologies such as PCR, enzyme digestion, gel recovery, ligation transformation, colony PCR or enzyme digestion identification, the target gene was subcloned into mammalian cell expression vectors, and the target gene with the recombinant expression vectors was further sequenced and analyzed. After the sequence was verified to be correct, a medium and large amount of endotoxin-free expression plasmids were prepared, and transiently transfected HEK293 cells for protein expression. After 7 days of culture, the cell culture was collected and affinity purified using a Ni SEPHAROSE™ column (GE), and the quality of the resulting protein samples was determined using SDS-PAGE and SEC-HPLC standard analysis techniques to be up to standard. After the quality determination was complete, the biotinylated human IL-17RA-His protein samples were labeled and obtained with the commercial kit EZ-Link® Sulfo-NHS-LC-Biotinylation of Thermo scientific, and the specific preparation method was performed according to the manual of the kit.

Figure 14:
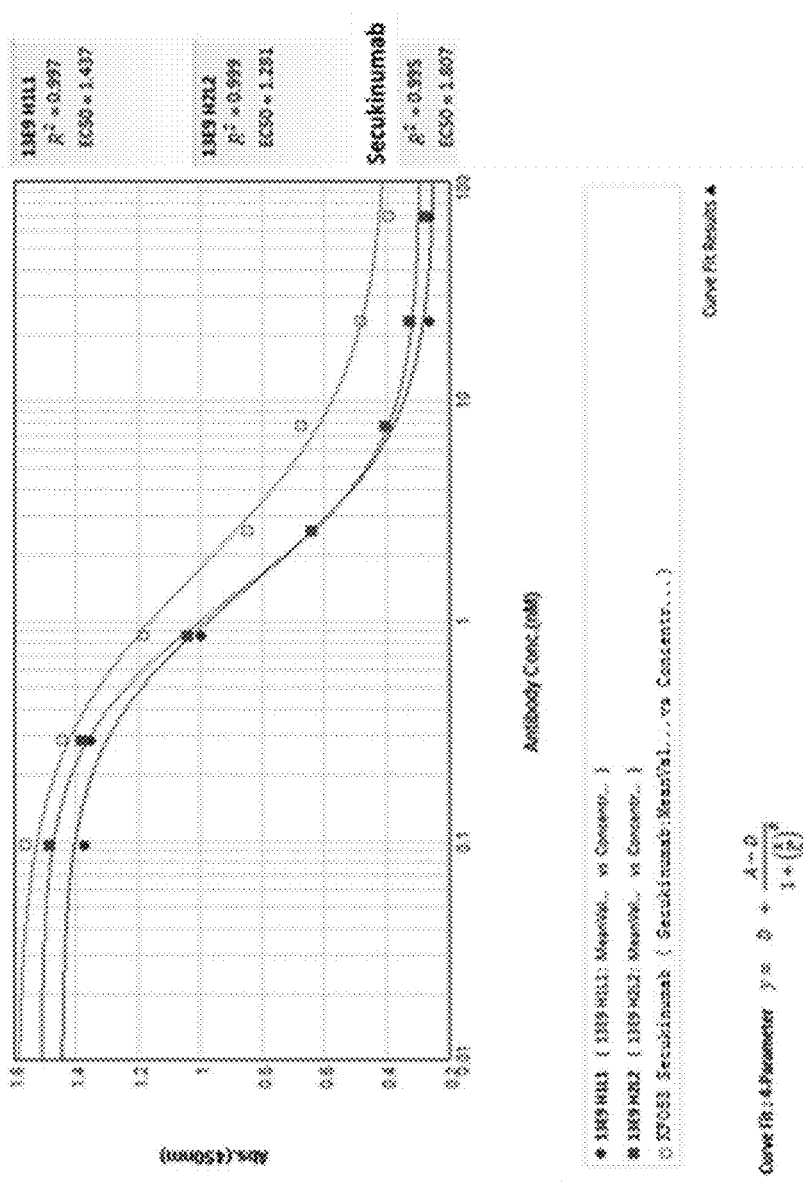
FIG. 14: detection of the activity of antibodies 13E9 H1L1 and 13E9 H2L2 competing with receptor IL17RA-His (biotin) for binding by competitive ELISA method. The marketed drug Secukinumab is used as a positive control.
Figure 15:
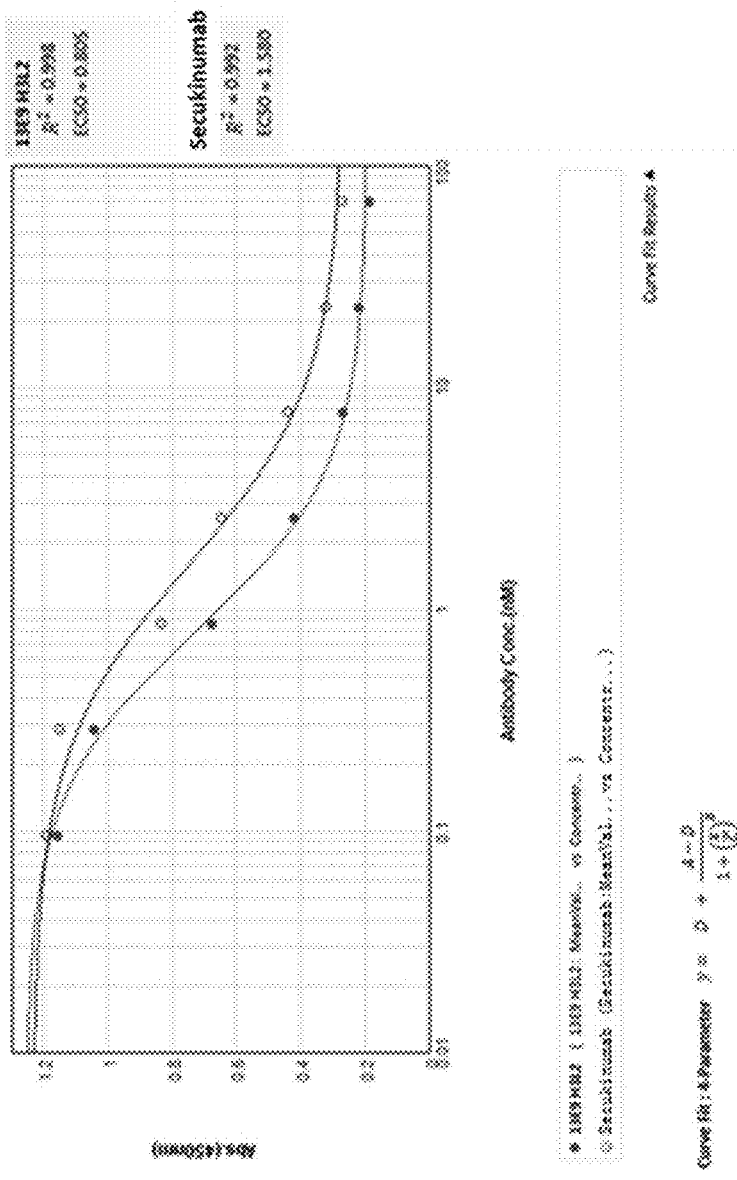
FIG. 15: detection of the activity of antibody 13E9 H3L2 competing with receptor IL17RA-His (biotin) for binding by competitive ELISA method. The marketed drug Secukinumab is used as a positive control.

ELISA: IL17A-His was added to the microplate and incubated at 4° C. overnight; after blocking with 1% BSA in PBST at 37° C. for 2 h, antibodies are added respectively, and the antigen and the antibody reacted at room temperature for 10 min; then the receptor IL17RA-His (biotin) was added which was mixed well with the antibody at a volume ration of 1:1 and incubated at 37° C. for 30 min; and SA-HRP (KPL, 14-30-00) was added and incubated at 37° C. for 30 min; and then the color reaction was performed with TMB (Neogen, 308177) for 5 min, and the absorbance at 450 nm was detected in a microplate reader. The obtained experimental data were analyzed and processed with Soft-Max Pro 6.2.1 software, and the 4-parameter fitted curve was plotted for analysis with the antibody concentration as the abscissa and the absorbance value as the ordinate. The experimental results are shown in FIG. 14, FIG. 15, and Table 5 and Table 6 below.

TABLE 5 detection results of the activity of 13E9 H1L1and
13E9 H2L2 competing with the receptor IL17RA-His
(biotin) for binding to the antigen IL17A-His

| Antibody concentration/ gradient | Antigen coating: IL17A-His (20150213) 0.5 µg/mL | | | | | |
|---|---|---|---|---|---|---|
| | 13E9 H1L1 | | 13E9 H2L2 | | Secukinumab | |
| 10 µg/mL | 0.273 | 0.249 | 0.274 | 0.290 | 0.402 | 0.392 |
| 1:3 | 0.299 | 0.220 | 0.313 | 0.339 | 0.469 | 0.502 |
| 1:9 | 0.418 | 0.379 | 0.431 | 0.379 | 0.642 | 0.708 |
| 1:27 | 0.673 | 0.610 | 0.646 | 0.636 | 0.842 | 0.855 |
| 1:81 | 0.986 | 1.008 | 1.011 | 1.069 | 1.169 | 1.201 |
| 1:243 | 1.342 | 1.362 | 1.428 | 1.331 | 1.418 | 1.468 |
| 1:729 | 1.363 | 1.375 | 1.447 | 1.519 | 1.467 | 1.657 |
| 0 | 1.495 | 1.406 | 1.429 | 1.561 | 1.610 | 1.495 |
| Receptor | IL17RA-His(bio) 0.1 µg/mL | | | | | |
| $EC_{50}$(nM) | 1.437 | | 1.281 | | 1.807 | |

TABLE 6 detection results of the activity of 13E9 H3L2 competing with the receptor IL17RA-His (biotin) for binding to the antigen IL17A-His

| Antibody concentration/ gradient | Antigen coating: IL17A-His 0.5 μg/mL | | | |
| | 13E9 H3L2 | | Secukinumab | |
| --- | --- | --- | --- | --- |
| 10 μg/mL | 0.193 | 0.182 | 0.263 | 0.282 |
| 1:3 | 0.231 | 0.206 | 0.318 | 0.327 |
| 1:9 | 0.265 | 0.267 | 0.419 | 0.462 |
| 1:27 | 0.424 | 0.415 | 0.630 | 0.663 |
| 1:81 | 0.725 | 0.627 | 0.813 | 0.859 |
| 1:243 | 1.069 | 1.018 | 1.120 | 1.182 |
| 1:729 | 1.218 | 1.095 | 1.133 | 1.250 |
| 0 | 1.184 | 1.334 | 1.182 | 1.232 |
| Receptor | IL17RA-His(bio) 0.1 μg/mL | | | |
| $EC_{50}$ (nM) | 0.805 | | 1.580 | |

The experimental results show that the antibodies 13E9 H1L1, 13E9 H2L2 and 13E9 H3L2 all can effectively block the binding of the receptor IL17RA-His (biotin) to the antigen IL17A-His, and the blocking efficiency is dose-dependent. Under the same experimental conditions, the EC50 of 13E9 H1L1 competing with IL17AR-His (biotin) for binding to IL17A-His is 1.437 nM, the EC50 of 13E9 H2L2 competing with IL17AR-His (biotin) for binding to IL17A-His is 1.281 nM, and the EC50 of the positive control drug Secukinumab for the same target competing with IL17AR-His (biotin) for binding to IL17A-His is 1.807 nM (Table 5, FIG. 14); the EC50 of 13E9 H3L2 competing with IL17AR-His (biotin) for binding to IL17A-His is 0.805 nM, and the EC50 of the marketed drug Secukinumab for the same target competing with IL17AR-His (biotin) for binding to IL17A-His is 1.580 nM (Table 6, FIG. 15).

The above experimental results show that under the same experimental conditions, the $EC_{50}$ values of 13E9 H1L1, 13E9 H2L2 and 13E9 H3L2 competing with IL17AR-His (biotin) for binding to IL17A-His are all smaller than those of the marketed control drug Secukinumab for the same target, indicating the activity of 13E9 H1L1, 13E9 H2L2 and 13E9 H3L2 competing with IL17AR-His (biotin) for binding to IL17A-His is better than that of the marketed drug Secukinumab for the same target.

Example 9: Detection of the Binding Activity of the Antibodies 2G2 H1L1, 2G2 H2L2 and 2G2 H3L3 to the Antigen with an ELISA Method 1. The binding activity of the antibodies 2G2 H1L1, 2G2 H2L2 and 2G2 H3L3 to the antigen IL17A-His is detected with an indirect ELISA.

Experimental steps: IL17A-His was added to the microplate and incubated at 4° C. overnight; after blocking with 1% BSA in PBS at 37° C. for 2 h, antibodies were added respectively, and incubated at 37° C. for 30 min; and Goat Anti Human IgG (H+L)-HRP (Jackson, 109-035-088) was added and incubated at 37° C. for 30 min; and then the color reaction was performed with TMB (Neogen, 308177) for 5 min, and the absorbance at 450 nm was detected in a microplate reader. The obtained experimental data were analyzed and processed with SoftMax Pro 6.2.1 software, and the 4-parameter fitted curve was plotted for analysis with the antibody concentration as the abscissa and the absorbance value as the ordinate.

Figure 16:
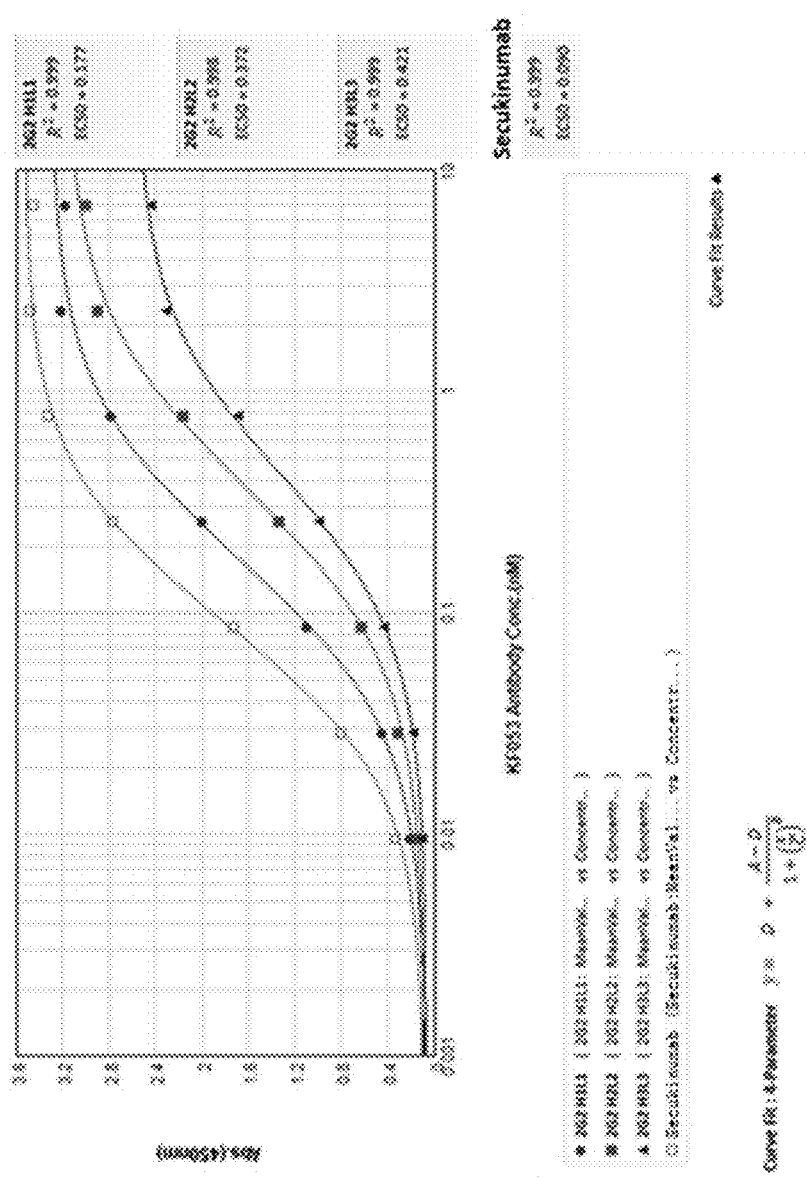
FIG. 16: detection of the binding activity of antibodies 2G2 H1L1, 2G2 H2L2 and 2G2 H3L3 to antigen IL17A-His by indirect ELISA method. The marketed drug Secukinumab is used as a positive control.

The experimental results are shown in FIG. 16 and Table 7 below. Wherein, the binding $EC_{50}$ of 2G2 H1L1 is 0.177 nM, the binding $EC_{50}$ of 2G2 H2L2 is 0.372 nM, and the binding 50 of 2G2 H3L3 is 0.421 nM.

TABLE 7 detection results of the binding of 2G2 H1L1, 2G2 H2L2 and 2G2 H3L3 to the antigen IL17A-His

| Antibody concentration/ gradient | Antigen coating: IL17A-His, 1 μg/mL | | | | | | | |
| | 2G2 H1L1 | | 2G2 H2L2 | | 2G2 H3L3 | | Secukinumab | |
| --- | --- | --- | --- | --- | --- | --- | --- | --- |
| 1 μg/mL | 3.220 | 3.135 | 3.030 | 2.960 | 2.485 | 2.384 | 3.448 | 3.448 |
| 1:3 | 3.284 | 3.149 | 2.899 | 2.886 | 2.311 | 2.314 | 3.477 | 3.478 |
| 1:9 | 2.820 | 2.747 | 2.199 | 2.126 | 1.693 | 1.703 | 3.320 | 3.331 |
| 1:27 | 2.020 | 1.969 | 1.348 | 1.328 | 0.982 | 1.002 | 2.768 | 2.764 |
| 1:81 | 1.113 | 1.075 | 0.638 | 0.624 | 0.439 | 0.440 | 1.761 | 1.689 |
| 1:243 | 0.469 | 0.426 | 0.261 | 0.350 | 0.188 | 0.186 | 0.807 | 0.806 |
| 1:729 | 0.224 | 0.188 | 0.131 | 0.148 | 0.113 | 0.102 | 0.337 | 0.326 |
| 0 | 0.061 | 0.057 | 0.058 | 0.068 | 0.063 | 0.060 | 0.062 | 0.060 |
| $EC_{50}$ (nM) | 0.177 | | 0.372 | | 0.421 | | 0.090 | |

The experimental results show that the antibodies 2G2 H1L1, 2G2 H2L2 and 2G2 H3L3 all can effectively bind to the antigen IL17A-His, and their binding efficiency is dose-dependent.

2. The activity of antibodies 2G2 H1L1, 2G2 H2L2 and 2G2 H3L3 competing with the receptor IL17A-His (biotin) for binding to the antigen IL17A-His was detected by competitive ELISA.

Experimental steps: IL17A-His was added to the microplate and incubated at 4° C. overnight; after blocking with 1% BSA in PBST at 37° C. for 2 h, antibodies were added respectively, and the antigen and the antibody reacted at room temperature for 10 min; then the receptor IL17RA-His (biotin) was added which is mixed well with the antibody at a volume ration of 1:1 and incubated at 37° C. for 30 min; and SA-HRP (KPL, 14-30-00) was added and incubated at 37° C. for 30 min; and then the color reaction was performed with TMB (Neogen, 308177) for 5 min, and the absorbance at 450 nm was detected in a microplate reader. The obtained experimental data were analyzed and processed with Soft-Max Pro 6.2.1 software, and the 4-parameter fitted curve was plotted for analysis with the antibody concentration as the abscissa and the absorbance value as the ordinate.

Figure 17:
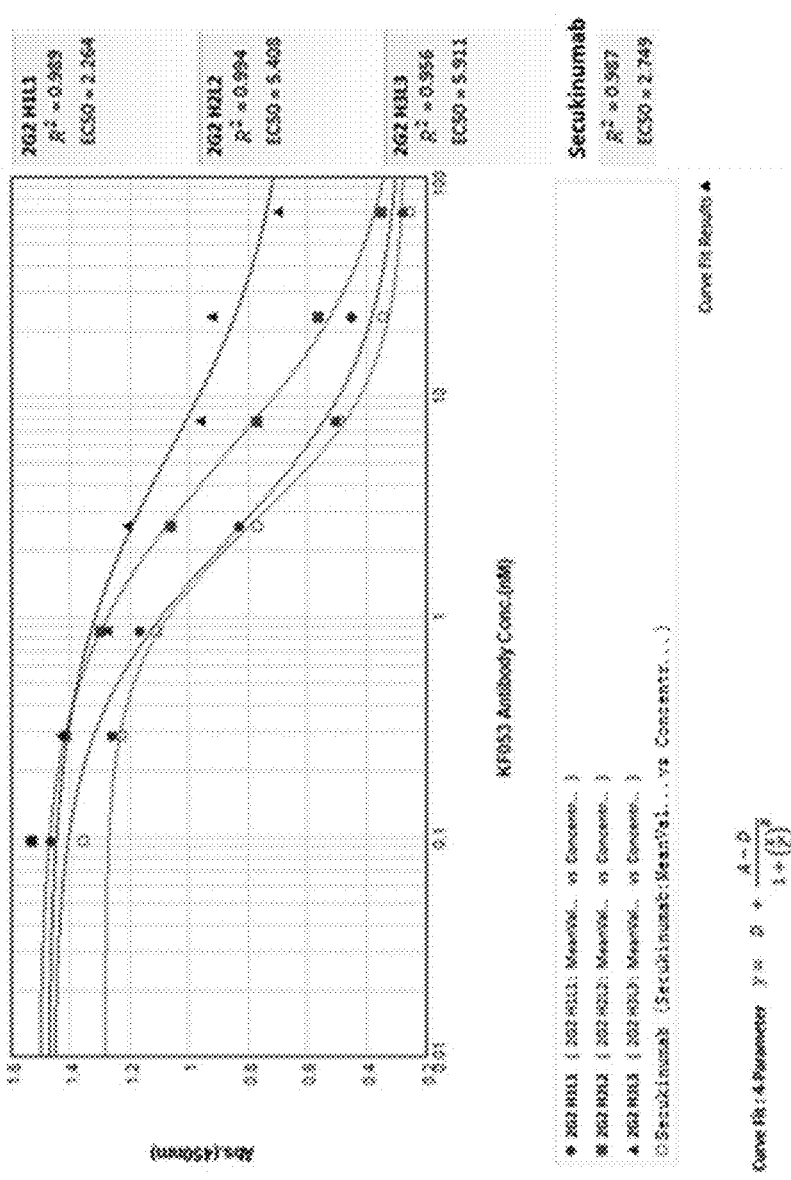
FIG. 17: detection of the activity of antibodies 2G2 H1L1, 2G2 H2L2 and 2G2 H3L3 competing with the receptor IL17A-His (biotin) for binding to antigen IL17A-His by competitive ELISA method. The marketed drug Secukinumab is used as a positive control.

The experimental results are shown in FIG. 17 and Table 8 below. Wherein, the blocking $EC_{50}$ of 2G2 H1L1 is 2.264 nM, the blocking $EC_{50}$ of 2G2 H2L2 is 5.408 nM, and the blocking $EC_{50}$ of 2G2 H3L3 is 5.911 nM (FIG. 17, Table 8).

TABLE 8 detection results of the activity of 2G2 H1L1, 2G2 H2L2 and 2G2 H3L3 competing with the receptor IL17RA-His (biotin) for binding to the antigen IL17A-His

| Antibody concentration/ | Antigen coating: IL17A-His 0.5 μg/mL | | | | | | | |
|---|---|---|---|---|---|---|---|---|
| gradient | 2G2 H1L1 | | 2G2 H2L2 | | 2G2 H3L3 | | Secukinumab | |
| 10 μg/mL | 0.285 | 0.272 | 0.337 | 0.366 | 0.680 | 0.718 | 0.247 | 0.267 |
| 1:3 | 0.417 | 0.485 | 0.500 | 0.623 | 0.971 | 0.876 | 0.333 | 0.361 |
| 1:9 | 0.506 | 0.502 | 0.785 | 0.751 | 0.971 | 0.954 | 0.478 | 0.507 |
| 1:27 | 0.891 | 0.763 | 1.087 | 1.038 | 1.242 | 1.178 | 0.758 | 0.784 |
| 1:81 | 1.162 | 1.167 | 1.286 | 1.309 | 1.246 | 1.312 | 1.088 | 1.135 |
| 1:243 | 1.231 | 1.281 | 1.423 | 1.402 | 1.398 | 1.466 | 1.272 | 1.184 |
| 1:729 | 1.453 | 1.472 | 1.464 | 1.596 | 1.607 | 1.466 | 1.392 | 1.324 |
| 0 | 1.455 | 1.425 | 1.494 | 1.424 | 1.470 | 1.340 | 1.170 | 1.230 |
| Receptor | IL17RA-His (biotin) :0.1 μg/mL | | | | | | | |
| $EC_{50}$ (nM) | 2.264 | | 5.408 | | 5.911 | | 2.749 | |

The experimental results show that the antibodies 2G2 H1L1, 2G2 H2L2, and 2G2 H3L3 all can effectively block the binding of the receptor IL17RA-His (biotin) to the antigen IL17A-His, and the blocking efficiency is dose-dependent.

Example 10: Mixed Human Embryonic Fibroblast Reaction: Secretion of Cytokine IL-6

MRC 5 (purchased from the Cell Center of the Chinese Academy of Sciences) cells were plated into a 96-well plate with 5000 cells/well and cultured overnight. A mixture of IL-17 and antibody (hIgG as a control) incubated at 37° C. for 20 min was added to the MRC 5 cells and cultured for 48 h. After 48 h of culturing, the cell supernatant was collected, and the amount of IL-6 secreted was detected by an ELISA kit (purchased from Dakewe Corporation).

Figure 18:
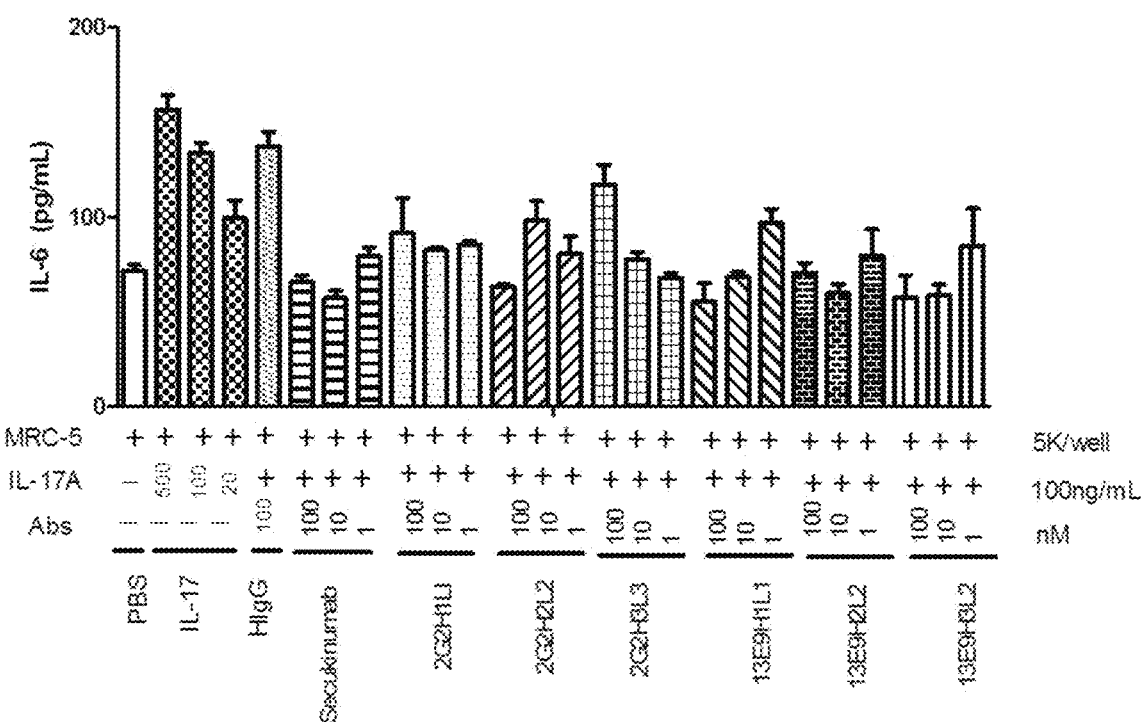
FIG. 18: effect of antibodies 13E9 H1L1, 13E9 H2L2 and 13E9 H3L2 as well as 2G2 H1L1, 2G2 H2L2 and 2G2 H3L3 on the secretion of cytokine IL-6 by mixed lymphocytes.

MRC 5 cells were mixed and cultured with 13E9 H1L1, 13E9 H2L2, 13E9 H3L2, 2G2 H1L1, 2G2 H2L2 or 2G2 H3L3 (1 nM, 10 nM, 100 nM) and Secukinumab (1 nM, 10 nM, 100 nM), respectively, and the detection results of secreted IL-6 are shown in FIG. 18.

It can be seen from FIG. 18 that 13E9 H1L1, 13E9 H2L2, 13E9 H3L2, and 2G2 H2L2 all can effectively reduce the IL-6 secretion of MRC 5 cells induced by IL-17, wherein:

the effect of 13E9 H1L1 antibody on inhibiting IL-6 secretion at a concentration of 100 nM is better than that of the control antibody Secukinumab at the same dose, and the inhibitory effect on IL-6 secretion at a concentration of 10 nM is equivalent to that of the control antibody Secukinumab at a concentration of 100 nM;

the effects of 13E9 H2L2 antibody on inhibiting IL-6 secretion at concentrations of 1 nM, 10 nM and 100 nM all are equivalent to that of the control antibody Secukinumab at the same dose;

the inhibitory effects of 13E9 H3L2 antibody on IL-6 secretion at concentrations of 10 nM and 100 nM all are better than that of the control antibody Secukinumab at the same dose, and the effect at a concentration of 1 nM is equivalent to that of the control antibody Secukinumab;

the effects of 2G2 H2L2 antibody on inhibiting IL-6 secretion at concentrations of 1 nM and 100 nM all are equivalent to that of the control antibody Secukinumab;

the effect of 2G2 H3L3 on inhibiting IL-6 secretion at a concentration of 1 nM is better than that of the control antibody Secukinumab at the same dose.

The above results show that in a mixed human embryonic fibroblast reaction in vitro, the biological activity of the antibodies of the present invention in blocking the IL-17A-mediated secretion of IL-6 is better than or at least equivalent to that of the marketed drug Secukinumab for the same target.

Example 11: Effect of the Antibody Drug 13E9 H3L2 on Epidermal Thickness of the C57BL/6 Mouse Psoriasis Model C57BL/6 mice were divided into 5 groups with 8 mice in each.

(1) Modeling:

normal group, C57BL/6 mice were injected intradermally with normal saline on the smooth back for 6 consecutive days from day 1 to day 6, 25 μL/mouse;

the remaining groups of mice were injected intradermally with a recombinant human IL-17A from day 1 to day 4, 2 μg/25 μL/mouse, and were injected intradermally with the recombinant human IL-17A from day 5 to day 6, 5 μg/25 μL/mouse.

(2) Specific grouping and administration:

normal group: normal saline, administered at a dose of 0 mg/kg, 3 times a week for a total of 3 times;

model group: negative isotype control, administered at a dose of 50 mg/kg, 3 times a week for a total of 3 times;

Secukinumab group: Secukinumab, administered at a dose of 50 mg/kg, 3 times a week for a total of 3 times;

13E9 H3L2 high dose group: administered at a dose of 50 mg/kg, 3 times a week for a total of 3 times;

13E9 H3L2 low dose group: administered at a dose of 10 mg/kg, 3 times a week for a total of 3 times.

Each group was administered subcutaneously 3 times, namely 1 day before the modeling, modeling day 3 and modeling day 6, respectively.

On day 7, the skins of the injection sites on the backs of the mice were fixed to make pathological sections and measure the epidermal thickness.

Figure 19:
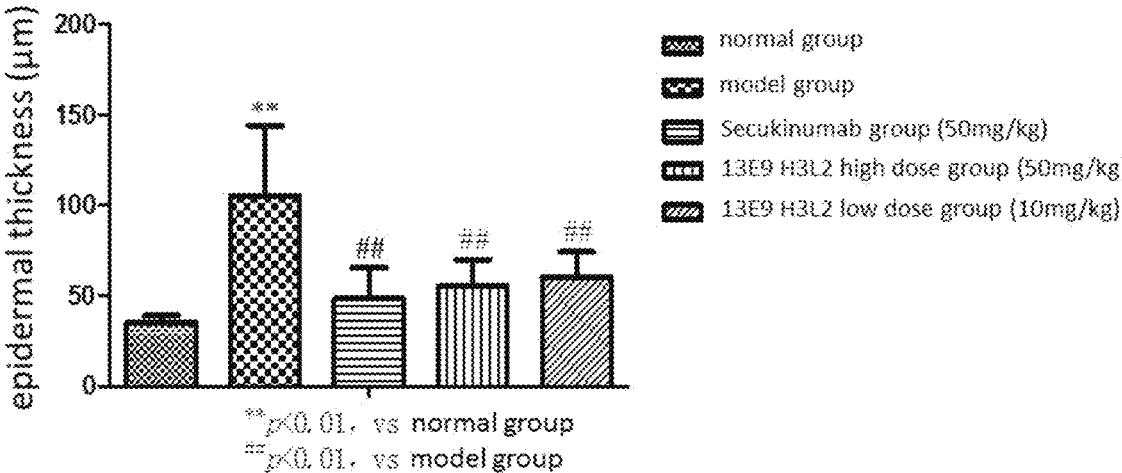
FIG. 19: effect of the antibody drug 13E9 H3L2 on epidermal thickness of the C57BL/6 mouse model with psoriasis.

The experimental results are shown in FIG. 19.

The results show that statistically, the epidermal thickness of the Secukinumab group (50 mg/kg), the 13E9 H3L2 high dose group (50 mg/kg) and the 13E9 H3L2 low dose group (10 mg/kg) was significantly smaller than that of the model group (P<0.01).

The results show that the antibody 13E9 H3L2 (50 mg/kg) shows statistically significant inhibitory effect on epidermal thickness in a C57BL/6 mouse psoriasis model, and has the same efficacy as Secukinumab (50 mg/kg); the inhibitory effect of 13E9 H3L2 (10 mg/kg) on epidermal thickness is also statistically significant.

Although specific embodiments of the present invention have been described in detail, those skilled in the art will understand. Various modifications and substitutions can be made to those details according to all the teachings that have been disclosed, and these changes are all within the protection scope of the present invention. The full scope of the present invention is given by the appended claims and any equivalent thereof.

What is claimed is:

1. An anti-interleukin-17A (anti-IL-17A) monoclonal antibody or an antigen-binding fragment thereof comprising:

a) a heavy chain variable region (VH) comprising three complementarity determining regions (HCDRs):

HCDR1 having the amino acid sequence set forth in SEQ ID NO: 31,

HCDR2 having the amino acid sequence set forth in SEQ ID NO: 32, and

HCDR3 having the amino acid sequence set forth in SEQ ID NO: 33; and b) a light chain variable region (VL) comprising three CDRs (LCDRs):

LCDR1 having the amino acid sequence set forth in SEQ ID NO: 34,

LCDR2 having the amino acid sequence set forth in SEQ ID NO: 35, and

LCDR3 having the amino acid sequence set forth in SEQ ID NO: 36.

2. The anti-IL-17A monoclonal antibody or antigen-binding fragment thereof of claim 1, wherein the VH comprises the amino acid sequence set forth in SEQ ID NO: 2, and the VL comprises the amino acid sequence set forth in SEQ ID NO: 4.

3. The monoclonal antibody or antigen-binding fragment thereof of claim 1, wherein the VH comprises the amino acid sequence set forth in SEQ ID NO: 6, and the VL comprises the amino acid sequence set forth in SEQ ID NO: 8.

4. The monoclonal antibody or antigen-binding fragment thereof of claim 1, wherein the VH comprises the amino acid sequence set forth in SEQ ID NO: 10, and the VL comprises the amino acid sequence set forth in SEQ ID NO: 12.

5. The monoclonal antibody or antigen-binding fragment thereof of claim 1, wherein the VH comprises the amino acid sequence set forth in SEQ ID NO: 14, and the VL comprises the amino acid sequence set forth in SEQ ID NO: 12.

6. The anti-IL-17A monoclonal antibody or antigen-binding fragment thereof of claim 1, wherein the anti-IL-17A monoclonal antibody or antigen-binding fragment thereof is selected from an Fab, an Fab', an F(ab')2, an Fv, a single chain antibody, a humanized antibody, a chimeric antibody, and a diabody.

7. The anti-IL-17A monoclonal antibody or antigen-binding fragment thereof of claim 1, wherein the anti-IL-17A monoclonal antibody or antigen-binding fragment thereof comprises non-CDR regions derived from a species other than a mouse.

8. A conjugate comprising the anti-IL-17A monoclonal antibody or antigen-binding fragment thereof of claim 1 and a conjugated portion comprising a detectable label.

9. A reagent kit comprising the anti-IL-17A monoclonal antibody or antigen-binding fragment thereof of claim 1.

10. A pharmaceutical composition comprising the anti-IL-17A monoclonal antibody or antigen-binding fragment thereof of claim 1 and at least one pharmaceutically acceptable carrier.

* * * * *